(12) United States Patent
Nair et al.

(10) Patent No.: US 7,235,709 B1
(45) Date of Patent: Jun. 26, 2007

(54) TRANSGENIC ANIMALS WITH INCREASED SLOW-TWITCH MUSCLE FIBERS AND METHODS OF USING SUCH ANIMALS

(75) Inventors: K. Sreekumaran Nair, Rochester, MN (US); Laura J. Greenlund, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/977,458

(22) Filed: Oct. 29, 2004

Related U.S. Application Data

(60) Provisional application No. 60/516,245, filed on Oct. 31, 2003.

(51) Int. Cl.
| | |
|---|---|
| A01K 67/027 | (2006.01) |
| A01K 67/00 | (2006.01) |
| A01K 67/033 | (2006.01) |
| G01N 33/00 | (2006.01) |
| C12N 15/00 | (2006.01) |
| C12N 5/00 | (2006.01) |
| C12P 21/06 | (2006.01) |

(52) U.S. Cl. ............... 800/18; 800/3; 800/8; 800/9; 800/14; 800/21; 800/24; 800/25; 435/69.1; 435/320.1; 435/325; 435/455

(58) Field of Classification Search ............... None
See application file for complete search history.

(56) References Cited

U.S. PATENT DOCUMENTS 4,873,191 A 10/1989 Wagner et al.

OTHER PUBLICATIONS

Baldwin et al., 2001, J. Appl. Physiol. 90: 345-357.*
Verma and Weitzman, 2005, Ann. Rev. Biochem, 74:711-738.*
Bockamp et al., 2001, Physiol. Genomics 11:115-132.*
Bishop., 1996, Reproductive Nutrition and Development 36: 607-616.*
Rulicke and Hubischer, 2000, Experimental Physiology 85: 589-601.*
Holschneider et al., 2001, Int J. Devl. Neuroscience 18:615-618.*
Cox et al., 2003, Curr opinion in Genetics & Development, 13:278-283.*
Giannoukakis, 2002, Curr. Opin. Investig. Drugs., 3: 735-751.*
Goncalves, Bioessays, 2005, 27: 506-517.*
Gardlik et al., Med. Sci. Monit, 2005, 11:RA110-121.*
Balagopal et al., "Age effect on transcript levels and synthesis rate of muscle MHC and response to resistance exercise," *Am. J. Physiol. Endocrinol. Metab.*, 2001, 280:E203-E208.
Chow et al., "Folding of the Striated Muscle Myosin Motor Domain," *J. Biol. Chem.*, 2002, 277(39):36799-36807.
Cibelli et al., "Cloned Transgenic Claves Produced from Nonquiescent Fetal Fibroblasts," *Science*, 1998, 280:1256-1258.
Copeland et al., "Heated dorsal hand vein sampling for metabolic studies: a reappraisal," *Am. J. Physiol.*, 1992, 263:E1010-E1014.
Cussóet al., "Differences between glycogen biogenesis in fast- and slow-twitch rabbit muscle," *Biochim. Biophys. Acta.*, 2003, 1620:65-71.
Derave et al., "Muscle glycogen content affects insulin-stimulated glucose transport and protein kinase B activity," *Am. J. Physiol. Endocrinol. Metab.*, 2000, 279:E947-E955.
Gabriely et al., "Removal of Visceral Fat Prevents Insulin Resistance and Glucose Intolerance of Aging. An Adipokine-Mediated Process?" *Diabetes*, 2002, 51:2951-2958.
Giulian et al., "Improved Methodology for Analysis and Quantitation of Proteins on One-Dimensional Silver-Stained Slab Gels," *Anal. Biochem.*, 1983, 129:277-287.
Halvatsiotis et al., "Synthesis Rate of Muscle Proteins, Muscle Functions, and Amino Acid Kinetics in Type 2 Diabetes," *Diabetes*, 2002, 51:2395-2404.
Hood, "*Plasticity in Skeletal, Cardiac, and Smooth Muscle* Invited Review: Contractile activity-induced mitochondrial biogenesis in skeletal muscle," *J. Appl. Physiol.*, 2001, 90:1137-1157.
Levine et al., "Effect of hyperthyroidism on spontaneous physical activity and energy expenditure in rats," *J. Appl. Physiol.*, 2003, 94:165-170.
Lexell et al., "What is the cause of the ageing atrophy? Total number, size and proportion of different fiber types studied in whole vastus lateralis muscle from 15- to 83-year old men," *J. Neurol. Sci.*, 1988, 84:275-294.
Lo, "Transformation by Iontophoretic Microinjection of DNA: Multiple Integrations Without Tandem Insertions," *Mol. Cell. Biol.*, 1983, 3(10):1803-1814.
Marshall et al., "Germline Manipulation of Glucose Homeostasis via Alteration of Glucose Transporter Levels in Skeletal Muscle," *J. Biol. Chem.*, 1993, 268(25):18442-18445.
Nair et al., "Leucine incorporation into mixed skeletal muscle protein in humans," *Am. J. Physiol.*, 1988, 254:E208-E213.
Ogilvie and Feeback, "A Metachromatic Dye-ATPase Method for the Simultaneous Identification of Skeletal Muscle Fiber Types I, IIA, IIB and IIC," *Stain Technology*, 1990, 65(5):231-241.
Scarpulla, "Transcriptional activators and coactivators in the nuclear control of mitochondrial function in mammalian cells," *Gene*, 2002, 286:81-89.
Shulman et al., "Quantitation of Muscle Glycogen Synthesis in Normal Subjects with Non-Insulin-Dependent Diabetes by $^{13}$C Nuclear Magnetic Resonance Spectroscopy," *New Engl. J. Med.*, 1990, 322(4):223-228.
Shani et al., "Expression of the Rat Myosin Light-Chain 2 Gene in Transgenic Mice: Stage Specificity, Developmental Regulation, and Interrelation with the Endogenous Gene," *Mol. Cell. Biol.*, 1988, 8(2):1006-1009.

(Continued)

*Primary Examiner*—Sumesh Kaushal
*Assistant Examiner*—Kelaginamane T. Hiriyanna
(74) *Attorney, Agent, or Firm*—Fish & Richardson P.C.

(57) ABSTRACT

Transgenic non-human mammals over-expressing MHCI in skeletal muscle are provided herein, as are methods of using these transgenic non-human mammals for screening candidate compounds for treating type 2 diabetes, and methods for altering the ratio of MHCI to MHCII in a subject.

17 Claims, 18 Drawing Sheets

OTHER PUBLICATIONS

Shastry, "Gene disruption in mice: Models of development and disease," *Mol. Cell. Biochem.*, 1998, 181:163-179.

Short et al., "Impact of Aerobic Exercise Training on Age-Related Changes in Insulin Sensitivity and Muscle Oxidative Capacity," *Diabetes*, 2003, 52:1888-1896.

Srikakulam and Winkelmann, "Myosin II Folding Is Mediated by a Molecular Chaperonin," *J. Biol. Chem.*, 1999, 274(38):27265-27273.

Talmadge and Roy, "Electrophoretic separation of rat skeletal muscle myosin heavy-chain isoforms," *J. Appl. Physiol.*, 1993, 75(5):2337-2340.

Taylor et al., "A Questionnaire for the Assessment of Leisure Time Physical Activities," *J. Chron. Dis.*, 1978, 31:741-755.

Thompson et al., "Germ Line Transmission and Expression of a Corrected HPRT Gene Produced by Gene Targeting in Embryonic Stem Cells," *Cell*, 1989, 56:313-321.

Thorstensson and Karlsson, "Fatiguability and Fibre Composition of Human Skeletal Muscle," *Acta Physiol. Scand.*, 1976, 98:318-322.

Van der Putten et al., "Efficient insertion of genes into the mouse germ line via retroviral vectors," *Proc. Natl. Acad. Sci. USA*, 1985, 82:6148-6152.

Weiss and Leinwand, "The mammalian myosin heavy chain gene family," *Annu. Rev. Cell Dev. Biol.*, 1996, 12:417-439.

Weiss et al., "Organization of human and mouse skeletal myosin heavy chain gene clusters is highly conserved," *Proc. Natl. Acad. Sci. USA*, 1999, 96:2958-2963.

Wilmut et al., "Viable offspring derived from fetal and adult mammalian cells," *Nature*, 1997, 385(6619):810-813.

* cited by examiner

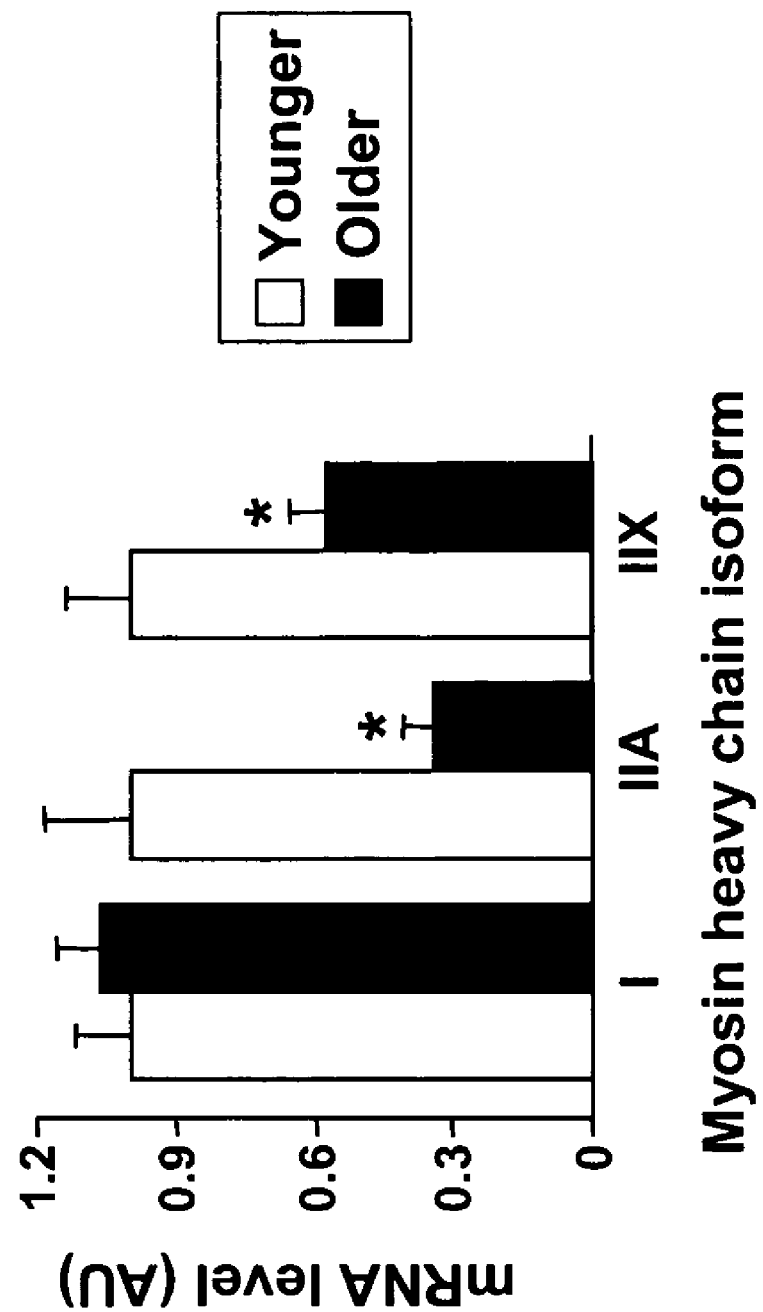

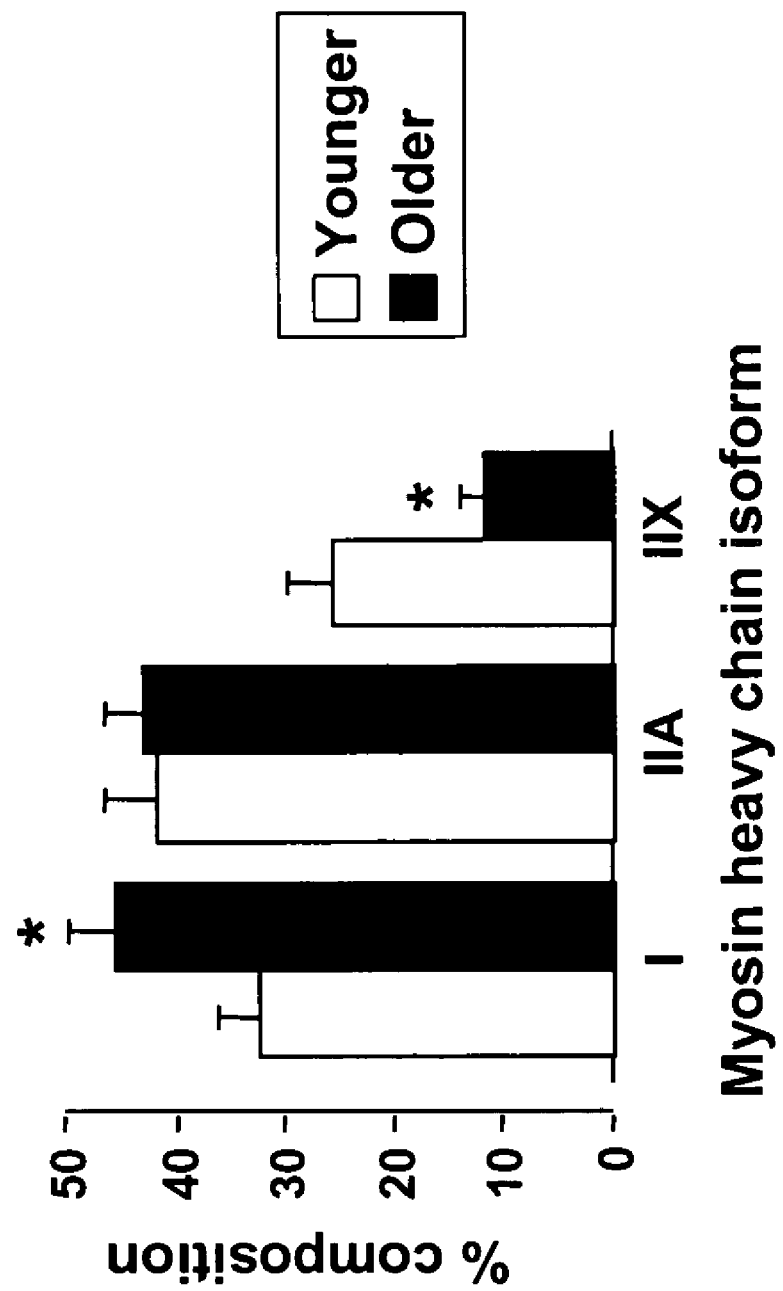

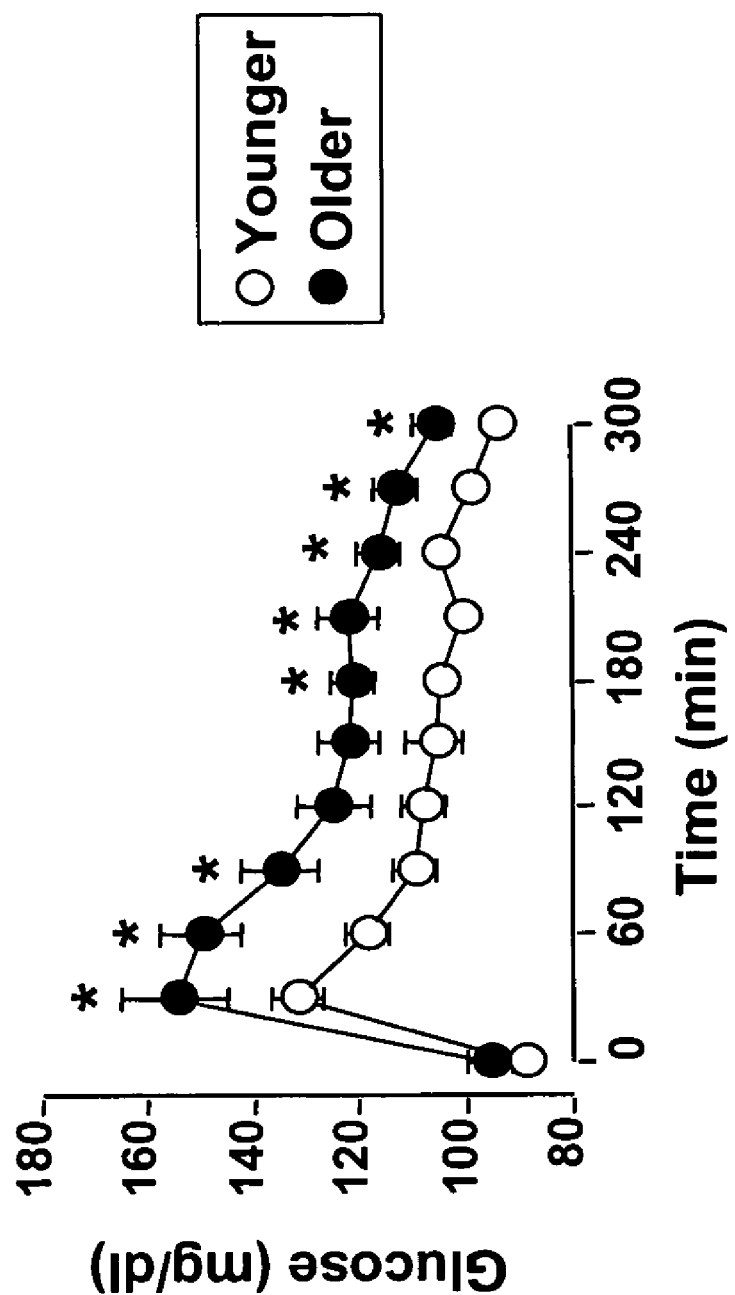

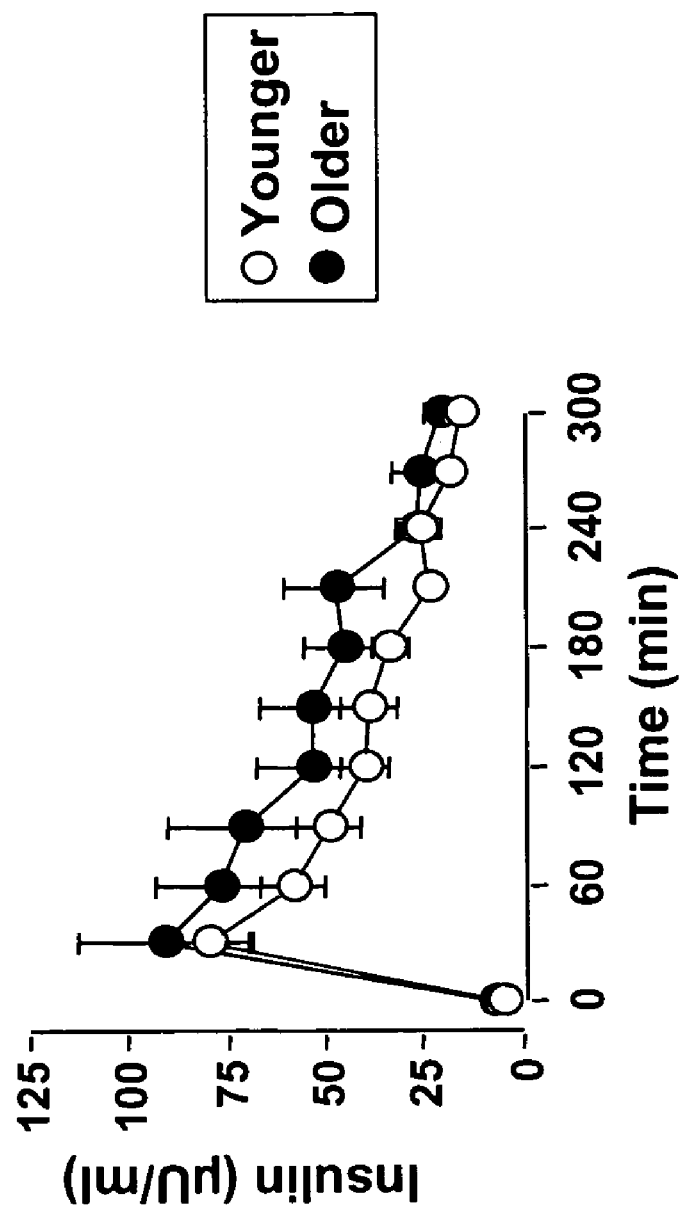

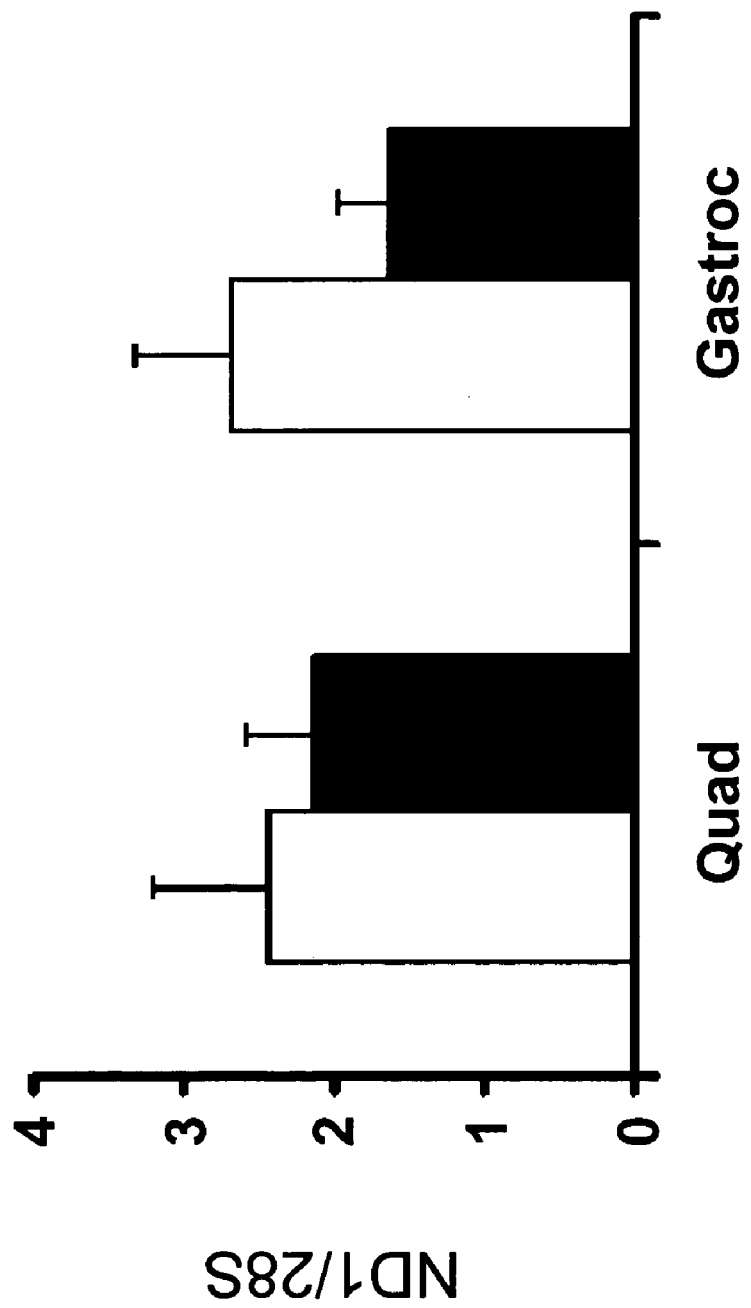

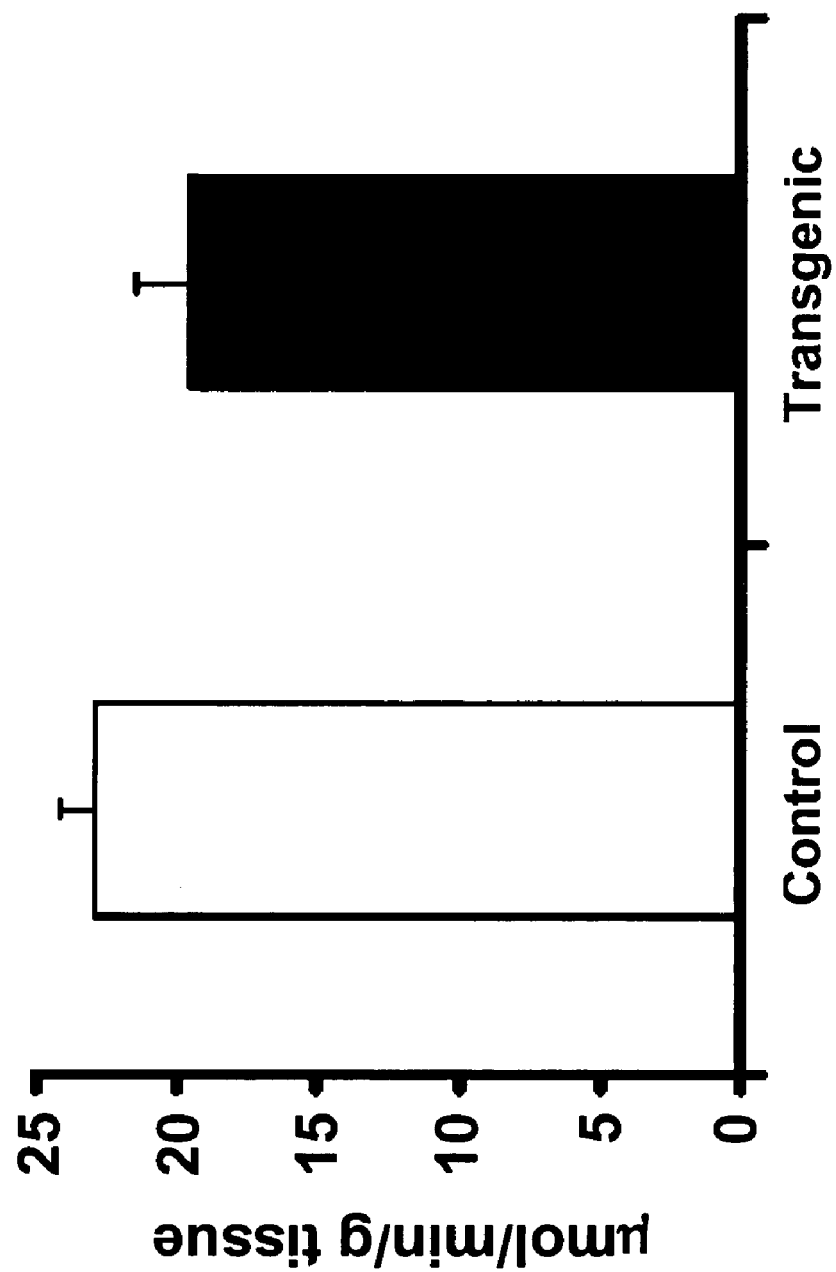

SEQUENCE LISTING

<160> NUMBER OF SEQ ID NOS: 10

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
aaggagaatc agaattagta tcagggtt                                      28

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
tgtactctgc tataaagaat aacgcgaat                                     29

<210> SEQ ID NO 3
<211> LENGTH: 21
<212> TYPE: DNA
<213> ORGANISM: Artificial Sequence
<220> FEATURE:
<223> OTHER INFORMATION: Probe

<400> SEQUENCE: 3
acgtagaata cgcagccggc c                                             21

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
aagaattccc gctcagtcat ggcggatcga gagat                              35

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
ccttgttctc tgttgcgtgc ttttcct                                       27

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
caaactggaa gacgagtgct cagagct                                       27

<210> SEQ ID NO 7
<211> LENGTH: 27

```
<212> TYPE: DNA
<213> ORGANISM: Artificial Sequence
<220> FEATURE:
<223> OTHER INFORMATION: Primer

<400> SEQUENCE: 7
ttgtcgaagt tcctctgctt cttgtcc                                          27

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
agaacgagat cgaggacctg atggtgg                                          27

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
tcacaggcat ccttagggtt gggtagc                                          27

<210> SEQ ID NO 10
<211> LENGTH: 59
<212> TYPE: DNA
<213> ORGANISM: Artificial Sequence
<220> FEATURE:
<223> OTHER INFORMATION: Primer

<400> SEQUENCE: 10
gcaagcttgc tacttgtcgt cgtccttgta gtcctcttca ttcaggccct tggcgccaa       59
```

TRANSGENIC ANIMALS WITH INCREASED SLOW-TWITCH MUSCLE FIBERS AND METHODS OF USING SUCH ANIMALS

CROSS-REFERENCE TO RELATED APPLICATIONS

This application claims priority from U.S. Provisional Application Ser. No. 60/516,245, filed Oct. 31, 2003.

STATEMENT AS TO FEDERALLY SPONSORED RESEARCH

Funding for the work described herein was provided in part by the National Institutes of Health, grant numbers AG 09531 and RR 00585. The federal government may have certain rights in the invention.

TECHNICAL FIELD

This invention relates to transgenic non-human animals that overexpress MHCI, methods for using the transgenic animals to screen candidate compounds for use in treating disease, and materials and methods for altering the ratio of slow-twitch muscle fibers to fast-twitch muscle fibers.

BACKGROUND

Approximately 17 million people in the United States, or 6.2% of the population, have diabetes. Diabetes is a disease in which the body either does not produce or does not properly use insulin, a hormone that regulates blood glucose levels. The cause of diabetes is not known, although both genetics and environmental factors such as obesity and lack of exercise appear to play roles.

The two most common types of diabetes are type 1 diabetes and type 2 diabetes. Type 1 diabetes [formerly called insulin-dependent diabetes mellitus (IDDM) or juvenile-onset diabetes] develops when the body's immune system destroys pancreatic beta cells, the only cells in the body that make insulin. This form of diabetes usually strikes children and young adults, who require exogenous insulin to survive. It is estimated that 5–10% of Americans diagnosed with diabetes have type 1 diabetes.

Approximately 90–95% of Americans who are diagnosed with diabetes have type 2 diabetes [formerly called non-insulin-dependent diabetes mellitus (NIDDM) or adult-onset diabetes]. Type 2 diabetes usually begins as insulin resistance, a disorder in which the cells do not use insulin properly. As the need for insulin rises, the pancreas gradually loses its ability to produce insulin. Type 2 diabetes is associated with obesity, family history of diabetes, prior history of gestational diabetes, impaired glucose tolerance, physical inactivity, race/ethnicity, and older age.

Impaired glucose tolerance (IGT) and impaired fasting glucose (IFG) are considered to be prediabetic conditions. IGT is a condition in which the blood glucose level is elevated (between 140 and 199 mg/dL in a 2-hour oral glucose tolerance test), but is not high enough to be classified as diabetes. IFG is a condition in which the fasting blood glucose level is elevated (between 110 and 125 mg/dL after an overnight fast) but is not high enough to be classified as diabetes. Studies suggest that IGT and IFG may be reversible. With an increasingly aged population, however, IGT and development of type 2 diabetes are emerging as major worldwide public health problems. The cause of age-related impaired glucose tolerance remains to be defined.

SUMMARY

The invention is based on the discovery that selective over-expression of MHCI in mouse skeletal muscle resulted in a substantial change in glucose metabolism and caused fat accumulation, indicating a link between muscle fiber type, glucose metabolism, and body composition. A predominance of slow-twitch muscle, e.g., as occurs with age in humans and other organisms, results in limited glycogen storage capacity, particularly after feeding. Without being bound by a particular mechanism, storage of glycogen in muscle is autoregulated such that when capacity has been reached, further storage is limited and more glucose is shunted toward the ATP production pathway. This can lead to an accumulation of glucose-6-phosphate, which may signal to the muscle cell that it is necessary to limit further glucose entry and, in turn, could lead to higher blood glucose concentrations. The presence of high blood glucose and insulin concentrations favors glucose entry into adipocytes and storage of this excess energy as fat, and subsequently results in further increases in insulin resistance.

The invention provides a mouse model of type 2 (non-insulin-dependent) diabetes. The invention also provides methods for using this model system to screen compounds for effectiveness in treating type 2 diabetes. Furthermore, the invention provides methods for altering the ratio of slow-twitch to fast-twitch muscle fibers in a subject.

In one aspect, the invention features a transgenic non-human mammal, the nucleated cells of which contain a transgene that includes a promoter operably linked to a nucleic acid encoding a myosin heavy chain-I (MHCI) polypeptide, wherein expression of the nucleic acid results in an increase in the number of slow-twitch muscle fibers in skeletal muscle of the non-human mammal as compared to the number of slow-twitch muscle fibers in skeletal muscle of corresponding non-transgenic, non-human mammals. The mammal can be a rodent (e.g., a mouse). The MHCI polypeptide can be a rodent (e.g., rat or mouse) MHCI polypeptide, and the promoter can be a myosin light chain promoter (e.g., an MLC2 promoter, and in particular, a mouse MLC2 promoter). The transgenic non-human mammal can display one or more symptoms or complications of diabetes (e.g., type 2 diabetes). The one or more symptoms or complications of diabetes can be selected from the group consisting of impaired glucose tolerance, insulin resistance, cardiovascular disorders, ketoacidosis, foot problems, skin problems, infection, slow wound healing, excessive thirst, frequent urination, blurred vision, and fatigue. The muscle mitochondrial content of the non-human transgenic mammal may not be significantly different from the muscle mitochondrial content of the corresponding non-transgenic, non-human mammals.

In another aspect, the invention provides a method of screening compounds for effectiveness in treating diabetes. The method can include (a) providing a candidate compound; (b) providing a non-human transgenic mammal, the nucleated cells of which contain a transgene, wherein the transgene includes a promoter operably linked to a nucleic acid encoding an MHCI polypeptide, wherein expression of the nucleic acid results in an increased ratio of type I muscle fibers to type II muscle fibers in skeletal muscle of the non-human mammal as compared to the ratio of type I muscle fibers to type II muscle fibers in skeletal muscle of corresponding non-transgenic, non-human mammals; (c) administering the candidate compound to the non-human transgenic mammal; and (d) monitoring the non-human transgenic mammal for one or more symptoms or complications of diabetes. The diabetes can be type 2 diabetes. The MHCI polypeptide can be a rodent (e.g., rat or mouse) MHCI polypeptide, and the promoter can be a myosin light chain promoter (e.g., an MLC2 promoter, and in particular, a mouse MLC2 promoter). The one or more symptoms or complications of diabetes can be selected from the group consisting of impaired glucose tolerance, insulin resistance, cardiovascular disorders, ketoacidosis, foot problems, skin problems, infection, slow wound healing, excessive thirst, frequent urination, blurred vision, and fatigue. The monitoring can include measuring glucose tolerance or measuring insulin resistance. The muscle mitochondrial content of the non-human transgenic mammal may not be significantly different from the muscle mitochondrial content of the corresponding non-transgenic, non-human mammals.

In another aspect, the invention features a method for decreasing the ratio of MHCI to MHCII in skeletal muscle fibers within a subject. The method can include administering to the subject a compound targeted to an MHCI nucleic acid or an MHCI polypeptide. The compound can result in reduced expression of MHCI. The compound can be an antisense nucleic acid. The compound can result in reduced incorporation of MHCI into muscle fibers. The subject can be a human.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1a is a graph showing mRNA levels of various MHC isoforms, as indicated, in human subjects. Open bars, younger subjects; solid bars, older subjects. *, P<0.01. FIG. 1b is a graph showing protein levels of various MHC isoforms, as indicated, in human subjects. Data represent the proportion of total myoHC represented by each isoform. Open bars, younger subjects; solid bars, older subjects. *, P<0.025. FIG. 1c is a graph showing blood glucose levels in human subjects after a large mixed meal. Open circles, younger subjects; filled circles, older subjects. *, P<0.05. FIG. 1d is a graph showing blood insulin levels in human subjects after a large mixed meal. Open circles, younger subjects; filled circles, older subjects. *, P<0.05.

FIG. 7a is a graph showing mitochondrial DNA copy number in the quadriceps and gastrocnemius/plantaris muscles in transgenic mice (n=7, solid columns) vs. control mice (n=5, open columns). FIG. 7c is a graph showing levels of mitochondrial citrate synthase activity in quadriceps of transgenic mice (n=8, solid columns) vs. control mice (n=5, open columns).

DETAILED DESCRIPTION

Figure 2A:
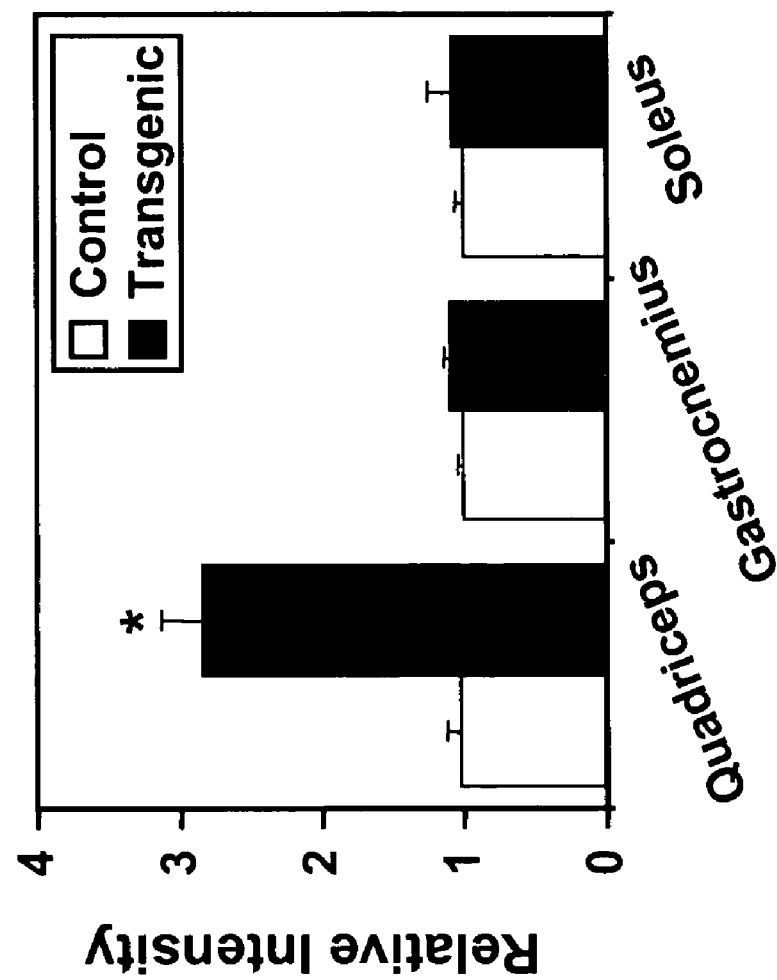
FIG. 2a is a graph showing relative MHCI levels in slow myoHCI transgenic mice (solid columns) vs. control mice (open columns), as determined by western blotting quantified by densitometry. Data are the mean±SEM of the relative intensity for the muscle groups indicated. *, P<0.0002.

Muscle is the major organ involved in disposal of glucose, especially following a meal. The invention is based on the relationship between muscle fiber type and glucose metabolism. The invention provides a transgenic mouse model of type 2 diabetes and methods for using this model system to screen compounds for effectiveness in treating type 2 diabetes. In the transgenic mice provided herein, the amount of slow-twitch muscle fibers is increased by selective overexpression of MHCI in skeletal muscle, which results in a substantial change in glucose metabolism and also causes fat accumulation.

Skeletal muscle in mammals such as humans and mice is composed of a mixture of slow-twitch (type 1) and fast-twitch (type 2) fibers. Slow-twitch fibers are less fatigable, rely heavily on oxidation of fuel for ATP production, are rich in enzymes for fat metabolism, and have less capacity to store glucose as glycogen. Fast-twitch fibers are more fatigable, rely more on glycolysis for ATP production, and have higher glycogen storage capacity. In some muscle groups, one type of fiber may be present in a higher proportion than the other type of fiber. The soleus muscle of the lower leg, for example, is composed mostly of slow-twitch fibers, whereas the quadriceps and gastrocnemius muscles in the leg are more mixed in fiber type. A predominance of slow-twitch muscle fiber also occurs with age in humans and other organisms. Gene expression studies, for example, demonstrated a reduction in fast-twitch myosin heavy chain isoforms IIa and IIx (MHCIIa and MHCIIx; also referred to herein as fast myoHC isoforms IIa and IIx) in older humans, whereas expression of slow-twitch myosin heavy chain I (MHCI; also referred to herein as slo myoHCI) was unaffected (Balagopal et al. (2001) *Physiol. Endocrinol. Metab.* 280:E203–E208). The relative increase in slow-twitch muscle fibers results in limited glycogen storage capacity, which in turn may lead to increased blood glucose concentrations. The presence of high blood glucose and insulin concentrations in turn favors entry of glucose into adipocytes and storage of this excess energy as fat, and subsequently results in further increases in insulin resistance. Thus, an increased ratio of MHCI to MHCII may be associated with diabetes. The transgenic mice provided here, which have an increased ratio of MHCI to MHCII, provide a model system for type 2 diabetes, and can be used to screen candidate compounds for effectiveness in treating type 2 diabetes. The invention also provides methods for decreasing the ratio of MHCI to MHCII in a subject. Such methods may be useful to, for example, treat type 2 diabetes.

Transgenes

The invention provides non-human mammals containing transgenes that include nucleotide sequences encoding MHCI polypeptides. A transgene is a nucleic acid, and can be RNA or DNA, including cDNA, genomic DNA, and synthetic (e.g., chemically synthesized) DNA. A transgene can be double-stranded or single-stranded (i.e., a sense or an antisense single strand). Typically, a transgene is double-stranded DNA that can integrate into the chromosomal DNA of a recipient non-human mammal. In addition, a transgene typically is a nucleic acid that is exogenous to the organism into which it is transferred (i.e., a transgene typically is produced outside the organism into which it is introduced). In some embodiments, an MHCI transgene contains MHCI nucleotide sequences that differ from those of the organism into which the transgene is introduced. For example, an MHCI transgene introduced into a mouse can contain a rat MHCI nucleic acid sequence, a human MHCI nucleic acid sequence, a mouse MHCI nucleic acid sequence that has been altered by, for example, deletion, insertion, or substitution, or a mouse MHCI nucleic acid sequence that is linked to a non-MHCI promoter [e.g., a mouse myosin light chain 2 (MLC2) promoter].

As used herein, the term "polypeptide" refers to any chain of amino acids, regardless of length or posttranslational modification (e.g., phosphorylation or glycosylation). An MHCI polypeptide can be, for example, a full-length MHCI polypeptide or a portion of a full-length MHCI polypeptide.

An MHCI transgene can include nucleotide sequences identical to those of nucleic acids encoding a wild-type MHCI polypeptide. For example, an MHCI transgene can contain a rat wild type MHCI nucleotide sequence (see, e.g., GenBank accession no. X15939). Alternatively, an MHCI transgene may contain codons other than wild-type codons which, due to the degeneracy of the genetic code, encode an MHCI polypeptide with an amino acid sequence identical to that of a wild-type MHCI polypeptide. Furthermore, an MHCI transgene may encode an MHCI polypeptide that is not identical to a wild type MHCI polypeptide due to the presence of, for example, one or more deletions, additions, or substitutions.

Transgenes can contain nucleotide sequences from more than one gene. For example, a transgene can include a first nucleotide sequence and a second nucleotide sequence, and may contain more nucleotide sequences (e.g., a third nucleotide sequence, a fourth nucleotide sequence, or more nucleotide sequences). Typically, a transgene includes a first nucleotide sequence encoding a polypeptide (e.g., a rodent MHCI polypeptide such as a rat or mouse MHCI polypeptide) and a second nucleotide sequence containing a promoter (e.g., an MLC2 promoter) to drive expression of the polypeptide. A transgene also can contain, for example, a third nucleotide sequence that encodes a selectable marker. The promoter that drives expression of the first polypeptide (e.g., MHCI) also may drive expression of the selectable marker, or expression of the selectable marker may be driven by a separate promoter. These nucleotide sequences may be arranged in any order relative to one another, and there can be a nucleotide spacer between any of the nucleotide sequences.

A transgene can be contained within a vector. As used herein, a "vector" is a replicon, such as a plasmid, phage, or cosmid, into which another DNA segment may be inserted so as to bring about the replication of the inserted segment. Thus, an MHCI transgene can be inserted into a vector in order to propagate the transgene prior to administration of the transgene to a non-human mammal. Furthermore, vectors containing MHCI transgenes can be used to generate transgenic non-human mammals, as described below.

Transgenic Non-Human Mammals

The invention features non-human mammals that include an MHCI transgene, as well as progeny and cells of such non-human mammals that retain the transgene. Transgenic non-human mammals can express an exogenous MHCI nucleic acid in addition to an endogenous MHCI (e.g., a transgenic non-human mammal can have an MHCI-containing transgene randomly integrated into its genome, while retaining its own MHCI alleles). Alternatively, an endogenous MHCI nucleic acid can be replaced by an exogenous MHCI nucleic acid (e.g., a transgene containing a variant MHCI nucleic acid) through homologous recombination. See Shastry (1998) *Mol. Cell. Biochem.* 181:163–179, for a review of gene targeting technology.

Transgenic non-human mammals can be, without limitation, farm animals such as pigs, goats, sheep, cows, horses and rabbits, rodents such as rats, guinea pigs and mice, and non-human primates such as baboons, monkeys and chimpanzees. Mice are particularly useful.

Various techniques known in the art can be used to introduce nucleic acid constructs into non-human mammals to produce founder lines of the transgenic non-human mammals. Such techniques include, without limitation, pronuclear microinjection (U.S. Pat. No. 4,873,191), retrovirus mediated gene transfer into germ lines (Van der Putten et al. (1985) *Proc. Natl. Acad. Sci. USA* 82:6148), gene targeting into embryonic stem cells (Thompson et al. (1989) *Cell* 56:313), electroporation of embryos (Lo (1983) *Mol. Cell. Biol.* 3:1803), and transformation of somatic cells in vitro followed by nuclear transplantation (Wilmut et al. (1997) *Nature* 385(6619):810–813). Typically, a transgene enters the nucleus of the cell into which it is introduced. Thus, transgenic non-human mammals generally contain a transgene in their nucleated cells.

In some embodiments, selectable markers can be used for positive or negative selection of a transgene. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus, which results in sensitivity to gancyclovir. Transgene constructs utilizing both positive and negative drug selection also can be used. For example, a construct can contain the aminoglycoside phosphotransferase gene and the TK gene. In this system, cells are selected that are resistant to G418 and sensitive to gancyclovir.

Skeletal muscle-specific expression of MHCI and MHCII in the transgenic non-human mammals provided herein can be assessed using standard techniques. Initial screening using, for example, Southern blot analysis or PCR techniques can indicate whether or not integration of the transgene has taken place. The level of mRNA expression of the transgene in tissues of transgenic non-human mammals can be assessed using techniques that include, without limitation, Northern blot analysis of tissue samples obtained from the animal, in situ hybridization analysis and reverse-transcriptase PCR (RT-PCR). Standard histochemical and immunohistochemical techniques also can be used to measure the level of MHCI or to measure the ratio of MHCI to MHCII in skeletal muscle of transgenic non-human mammals.

Expression of the MHCI transgene in the transgenic non-human mammals provided herein typically results in increased levels of MHCI in skeletal muscle fibers, as compared to the levels of MHCI in skeletal muscle fibers of corresponding non-transgenic mammals. Such transgenic non-human mammals, as a result, contain increased numbers of slow-twitch skeletal muscle fibers as compared to the number of slow-twitch skeletal muscle fibers in corresponding non-transgenic mammals. In addition, the ratio of MHCI to MHCII in skeletal muscle fibers is increased in such transgenic non-human mammals, as compared to the ratio of MHCI to MHCII in skeletal muscle fibers of corresponding non-transgenic mammals. Thus, the skeletal muscle of the transgenic non-human mammals provided herein contains an increased ratio of slow-twitch to fast-twitch muscle fibers, as compared to the ratio of slow-twitch to fast-twitch muscle fibers in skeletal muscle of corresponding non-transgenic mammals. Conversely, the ratio of MHCII to MHCI (and the ratio of fast-twitch to slow-twitch fibers) is decreased in skeletal muscle of the transgenic non-human mammals provided herein, as compared to the ratios of MHCII to MHCI and fast-twitch to slow-twitch fibers in corresponding non-transgenic mammals. Numbers of slow-twitch and fast-twitch fibers in skeletal muscle can be estimated using, for example, the methods disclosed in the Examples below.

As used herein, an "increase" in MHCI or in slow-twitch muscle fibers refers to any increase (e.g., a 5%, 10%, 20%, 25%, 50%, 75%, 90%, 100%, or more than 100% increase) in the amount of MHCI protein or the number of slow-twitch fibers in skeletal muscle. Similarly, an "increase" in the ratio of MHCI to MHCII or the ratio of slow-twitch to fast-twitch muscle fibers refers to any increase (e.g., a 5%, 10%, 20%, 25%, 50%, 75%, 90%, 100%, or more than 100% increase) in the ratio of MHCI to MHCII or the ratio of slow-twitch to fast-twitch muscle fibers. Typically, an increase in the amount of MHCI, in the ratio of MHCI to MHCII, or in the ratio of slow-twitch to fast-twitch fibers is as compared to the amount of MHCI, the ratio of MHCI to MHCII, or the ratio of slow-twitch to fast-twitch fibers in muscle (e.g., skeletal muscle fibers) of corresponding, non-transgenic (e.g., lacking the MHCI transgene) mammals. "Corresponding" non-transgenic mammals typically are of the same species as the transgenic mammal, but lack the MHCI transgene. The comparison can be made to, for example, the level of MHCI, the ratio of MHCI to MHCII, or the ratio of slow-twitch to fast-twitch fibers in muscle of a particular corresponding non-transgenic mammal, or to an average (e.g., "standard") level of MHCI, ratio of MHCI to MHCII, and/or ratio of slow-twitch to fast-twitch fibers in a population of corresponding non-transgenic mammals.

Transgenic non-human mammals that overexpress MHCI in skeletal muscle may display phenotypes that include symptoms and complications of diabetes (e.g., type 2 diabetes). Besides IGT and IFG, symptoms and complications of diabetes in humans include, for example, fatigue and/or nausea, frequent urination, excessive thirst, increased appetite, weight loss, blurred vision, irritability, slow healing of wounds or sores, recurring skin, mouth, or bladder infections, ketones in the urine, tingling and/or numbness in hands or feet, blood pressure consistently at or above 140/90, and HDL cholesterol less than 35 mg/dL or triglycerides greater than 250 mg/dL. The transgenic non-human mammals provided herein may exhibit any of these symptoms. As described below, for example, transgenic mice overexpressing MHCI in skeletal muscle can display impaired glucose tolerance, insulin resistance, and increased fat mass.

In one embodiment, non-human mammals are produced that lack an endogenous-MHCI nucleic acid (i.e., a knockout), and an MHCI transgene is introduced into the knockout non-human mammal. Nucleic acid constructs used for producing knockout non-human mammals can include a nucleic acid sequence encoding a selectable marker, which generally is used to interrupt the targeted exon site by homologous recombination. Typically, the selectable marker is flanked by nucleotide sequences homologous to the sequences flanking the desired insertion site. It is not necessary for the flanking sequences to be immediately adjacent to the desired insertion site.

To create non-human mammals having a particular gene inactivated in all cells, it is necessary to introduce a knockout construct into the germ cells (sperm or eggs, i.e., the "germ line") of the desired species. Genes or other nucleotide sequences can be introduced into germ cells by, for example, microinjection into the pronuclei of fertilized eggs followed by pronuclear fusion. Alternatively cultured embryonic stem cells can be transformed with a knockout construct and cells selected in which the MHCI gene is inactivated. Such cells then can be incorporated into an embryo, where they are capable of differentiating into all cell types, including germ cells, and thus can be employed to generate animals lacking an endogenous MHCI nucleic acid. In addition, direct microinjection of a knockout construct into eggs can be used to avoid the manipulations required to turn a cultured cell into an animal. In still another example, nuclear transplantation can be used to generate MHCI knockout animals. For example, fetal fibroblasts can be genetically modified such that they contain an inactivated MHCI gene, and then fused with enucleated oocytes. After activation of the oocytes, the eggs can be cultured to the blastocyst stage and implanted into a recipient. See, for example, Cibelli et al. (1998) *Science* 280:1256–1258.

Methods of Screening

Non-human mammals containing a transgene that encodes MHCI can be used in methods to screen compounds for effectiveness in treating type 2 diabetes. A candidate compound can be administered to a transgenic non-human mammal overexpressing MHCI in skeletal muscle, for example, and the transgenic mammal can be monitored for symptoms and/or complications of diabetes (e.g., impaired glucose tolerance, increased fasting glucose, increased insulin resistance, or increased body fat).

In one embodiment, diabetic symptoms and/or complications can be assessed in a first group of transgenic non-human mammals in the presence of the candidate compound, and compared with the same symptoms or complications in a corresponding transgenic control group in the absence of the candidate compound. In another embodiment, diabetic symptoms and/or complications can be assessed before and after administration of the candidate compound. A compound can be identified as effective for treating diabetes if (a) the symptoms or complications being assessed are reduced in animals treated with the candidate compound as compared to control, untreated animals, or (b) the symptoms or complications being assessed are reduced after treatment as compared to before treatment. Symptoms and complications of diabetes can be monitored using, for example, standard techniques. See, e.g., the Examples below.

Suitable candidate compounds can include biological macromolecules such as an oligonucleotide (RNA or DNA), a polypeptide of any length, a chemical compound, a mixture of chemical compounds, or an extract isolated from bacterial, plant, fungal, or animal matter. The concentration or amount of compound to be tested can depend on, for example, one or more of the following: the type of compound, the species, age, or size of the mammal, and in vitro test data.

Transgenic non-human mammals can be exposed to test compounds by any route of administration, including enterally and parenterally. For example, a compound can be administered parenterally through inhalation, or by intranasal, intravascular, intramuscular, or subcutaneous administration. Enteral routes include sublingual and oral administration. Compounds can be prepared for parenteral administration in the form of liquid solutions or suspensions; for oral administration in the form of tablets or capsules; or for intranasal administration in the form of powders, nasal drops, or aerosols. Compounds can be prepared for other routes of administration using standard techniques. Test compounds can be mixed with non-toxic excipients or carriers before administration. Inhalation formulations can include aqueous solutions containing, for example, polyoxyethylene-9-lauryl ether, glycocholate, or deoxycholate. Other formulations may contain sterile water or saline, or polyalkylene glycols such as polyethylene glycol.

Methods for Reducing MHCI Levels

The transgenic non-human mammals provided herein overexpress MHCI in skeletal muscle and display diabetic symptoms, indicating that reducing the amount of MHCI or the ratio of MHCI to MHCII (and thus reducing the ratio of slow-twitch to fast-twitch fibers) in skeletal muscle may be useful for treating diabetes. Thus, embodiments of the invention also provide methods for decreasing the amount of MHCI or the ratio of MHCI to MHCII in skeletal muscle of a subject (e.g., a mouse, a rat, a dog, a cat, a non-human primate, or a human). "Decreasing" the amount of MHCI or the ratio of MHCI to MHCII is meant to encompass any reduction (e.g., a 1%, 2%, 3%, 4%, 5%, 10%, 15%, 20%, 25%, 30%, 50%, 75%, 90%, or 100% reduction) in the amount of MHCI or the ratio of MHCI to MHCII in muscle fibers (e.g., skeletal muscle fibers) of a subject. Typically, such a decrease is as compared to a control level of MHCI or a control ratio of MHCI to MHCII. For example, the control can be the amount of MHCI or the ratio of MHCI to MHCII in the subject prior to treatment as described below. Alternatively, the control can be a standard amount of MHCI or a standard ratio of MHCI to MHCII, wherein the standard is measured in one or more subjects that typically have an increased ratio of slow-twitch to fast-twitch skeletal muscle fibers. For example, a standard ratio of MHCI to MHCII can be the average value measured in a population of subjects who are of older age (e.g., human subjects who are older than 50 years of age, older than 60 years of age, or older than 65 years of age).

The amount of MHCI or the ratio of MHCI to MHCII in muscle can be decreased by, for example, decreasing the expression of MHCI, or by inhibiting the incorporation of MHCI into muscle fibers. Methods of the invention can include administering to a subject a compound targeted to MHCI. As used herein, the term "compound targeted to MHCI" is meant to include compounds that directly or indirectly result in reduced expression of MHCI, or reduced incorporation of MHCI into muscle fibers. In some embodiments, for example, a compound can interact directly with an MHCI nucleic acid or an MHCI polypeptide. Alternatively, a compound can interact with a particular polypeptide, or with a nucleic acid encoding the particular polypeptide, that is involved in expression of MHCI or incorporation of MHCI into muscle fibers.

In one embodiment, the amount of MHCI in a subject can be reduced by administering to the subject an antisense nucleic acid targeted to MHCI. Such an antisense molecule (e.g., an antisense MHCI oligonucleotide) can target an endogenous MHCI nucleic acid (e.g., MHCI DNA or MHCI mRNA) so that expression of the endogenous MHCI gene is reduced in the subject. Alternatively, an antisense nucleic acid can be targeted to an endogenous nucleic acid encoding a polypeptide that regulates expression or function of MHCI.

An antisense nucleic acid can contain naturally occurring nucleotides and/or nucleotide analogs, and can specifically hybridize to a target nucleic acid (e.g., an MHCI nucleic acid or a nucleic acid encoding a polypeptide that regulates expression or function of MHCI). In some embodiments, an antisense oligonucleotide can contain naturally occurring nucleosides linked together by a non-natural internucleoside backbone (e.g., a backbone that includes phosphorothioate, phosphorodithioate, phosphotriester, aminoalkylphosphotriester, phosphinate, phosphoramidate, thionoalkylphosphotriester, or boranophosphate bonds). An antisense nucleic acid can be contained within a vector (e.g., an expression vector). An "expression vector" is a vector that includes expression control sequences, and an "expression control sequence" is a DNA sequence that controls and regulates the transcription and translation of another DNA sequence.

The nucleic acid sequence of an expression vector can include an antisense MHCI nucleic acid operably linked to one or more transcriptional regulatory elements. As used herein, "operably linked" means incorporated into a genetic construct so that expression control sequences effectively control expression of a coding sequence of interest. Examples of transcriptional regulatory elements include promoters, enhancers, and transcription terminating regions. A sequence is "operably linked" and "under the control" of transcriptional and translational control sequences in a cell when RNA polymerase is able to transcribe the sequence into mRNA.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

Expression vectors containing antisense MHCI nucleic acids can be used, for example, to transform or transfect either prokaryotic (e.g., bacteria) or eukaryotic (e.g., yeast, plant, insect, or mammalian) cells. For example, an expression vector containing an antisense MHCI nucleic acid can be administered to a subject with type 2 diabetes, for example. Once inside the cells of the subject, the antisense MHCI nucleic acid can be transcribed and can hybridize to endogenous MHCI nucleic acid sequences to prevent expression of the endogenous MHCI sequences.

The term "hybridization," as used herein, refers to hydrogen bonding, which can be Watson-Crick, Hoogsteen, or reversed Hoogsteen hydrogen bonding, between complementary nucleoside or nucleotide bases. For example, adenine and thymine, and guanine and cytosine, respectively, are complementary nucleobases (often referred to in the art simply as "bases") that pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides that can hydrogen bond with each other. Thus, "specifically hybridizable" is used to indicate a sufficient degree of complementarity or precise pairing such that stable and specific binding occurs between the oligonucleotide and the DNA or RNA target.

It is understood in the art that the sequence of an antisense nucleic acid need not be 100% complementary to that of its target nucleic acid to be specifically hybridizable. An antisense nucleic acid is specifically hybridizable when (a) binding of the nucleic acid to the target DNA or RNA molecule interferes with the normal function of the target DNA or RNA, and (b) there is sufficient complementarity to avoid non-specific binding of the antisense nucleic acid to non-target sequences under conditions in which specific binding is desired, i.e., under conditions in which in vitro assays are performed or under physiological conditions for in vivo assays or therapeutic uses.

Stringency conditions in vitro are dependent on temperature, time, and salt concentration (see, e.g., Sambrook et al., *Molecular Cloning, A Laboratory Manual*, second edition, Cold Spring Harbor Press, Plainview, N.Y., 1989). Typically, conditions of high to moderate stringency are used for specific hybridization in vitro, such that hybridization occurs between substantially similar nucleic acids, but not between dissimilar nucleic acids. Specific hybridization conditions can be, for example, hybridization in 5×SSC (0.75 M sodium chloride/0.075 M sodium citrate) for 1 hour at 40° C. with shaking, followed by washing 10 times in 1×SSC at 40° C. and 5 times in 1×SSC at room temperature. Antisense oligonucleotides that specifically hybridize to a target nucleic acid, for example, can be identified by recovering (e.g., by boiling) oligonucleotides from a pool of oligonucleotide/target hybridization duplexes and sequencing the recovered oligonucleotides.

In vivo hybridization conditions consist of intracellular conditions (e.g., physiological pH and intracellular ionic conditions) that govern the hybridization of antisense oligonucleotides with target sequences. In vivo conditions can be mimicked in vitro by relatively low stringency conditions. For example, hybridization can be carried out in vitro in 2×SSC (0.3 M sodium chloride/0.03 M sodium citrate), 0.1% SDS at 37° C. Alternatively, a wash solution containing 4×SSC, 0.1% SDS can be used at 37° C., with a final wash in 1×SSC at 45° C.

The specific hybridization of an antisense molecule with its target nucleic acid can interfere with the normal function of the target nucleic acid. For a target DNA, antisense technology can disrupt replication and transcription. For a target RNA, antisense technology can disrupt, for example, translocation of the RNA to the site of protein translation, translation of protein from the RNA, splicing of the RNA to yield one or more mRNA species, and catalytic activity of the RNA. The overall effect of such interference with target nucleic acid function is, in the case of a nucleic acid encoding MHCI, modulation of the expression of MHCI. In the context of the present invention, "modulation" means a decrease in the expression of a gene and/or a decrease in cellular levels of the protein encoded by a gene.

Similarly, RNA interference techniques can be used to reduce expression of MHCI or of polypeptides that modulate expression of MHCI. Such methods can include contacting an endogenous mRNA molecule with, for example, a small interfering RNA (siRNA). siRNA molecules typically are small, double-stranded RNAs that can interact with a target RNA molecule in a sequence-specific manner. siRNA duplexes can form siRNA-protein complexes with endonuclease activity, which can cleave target RNA molecules in the middle of the region covered by the siRNA duplex. Thus, delivery of siRNA duplexes can result in degradation of targeted mRNAs.

The invention also provides methods for reducing the ratio of MHCI to MHCII isoforms in skeletal muscle by inhibiting incorporation of MHCI polypeptides into muscle fibers. Such methods can involve, for example, interfering with proper folding of nascent MHCI polypeptides, or interfering with the association of nascent MHCI polypeptides with muscle fibers.

Each myosin molecule includes two myosin heavy chain polypeptides and a two pairs of dissimilar myosin light chain polypeptides, which must fold properly and associate in a particular manner. This process is thought to be mediated by a molecular chaperonin protein (Srikakulam and Winkelmann (1999) *J. Biol. Chem.* 274:27265–27273; and Chow et al. *J. Biol. Chem.* (2002) 277:36799–36807). Other proteins also may be involved in the folding and assembly of myosin molecules. Thus, the methods provided herein can include contacting one or more of the proteins involved in myosin folding and assembly with a compound that can prevent these processes from occurring properly. Typically, the contacting is in a subject. Useful compounds can include, for example, polypeptides (e.g., antibodies), or small molecules.

In addition, the assembly of muscle sarcomeres is a complex and dynamic process that involves a large number of proteins. Some of these proteins can interact with myosin and regulate its incorporation into muscle fibers. The methods provided herein thus can include contacting an MHCI polypeptide or a regulatory protein with a compound (e.g., an antibody or a small molecule) that can interfere with the interactions necessary for incorporation of MHCI into muscle fibers, thus reducing the ratio of MHCI to MHCII in the fibers.

The invention will be further described in the following examples, which do not limit the scope of the invention described in the claims.

EXAMPLES

Example 1

Materials and Methods

Human Subjects: Healthy men and women who exercised less than 30 minutes twice per week during the previous nine months were recruited. Health status was assessed by medical history, physical exam, blood chemistries (liver enzymes, creatinine, electrolytes and glucose), complete blood count, urinalysis, and electrocardiogram. Exclusion criteria included tobacco use, beta-blockers, diabetes or other endocrine disorders, and debilitating chronic illness.

All participants were provided with standardized diets, containing 55% carbohydrate, 30% fat, and 15% protein, for three days prior to their study. During this time subjects also were asked to refrain from any strenuous exercise but could otherwise maintain their normal daily activities. On the evening of the third day of outpatient meals, subjects were admitted to the GCRC for overnight stay. Studies were performed the following morning following an overnight fast.

For measurements of muscle myosin heavy chain expression, muscle samples from 22 young (age 21–38 years) and 32 older (60–87 years) people were used. Body composition and other characteristics of these participants have been published elsewhere (Short et al. (2003) *Diabetes* 52:1888–1896). Studies of the glucose and insulin response to a mixed meal were performed on two additional groups of 10 young (age 19–31 years) and 10 older (64–80 years) people. Participants in the meal studies had similar physical characteristics as those used for myosin heavy chain analysis.

Diabetic Subjects: Eight subjects with type 2 diabetes for an average of 8.5 years were studied. Six were on oral hypoglycemic agents and two were on diet alone. Body composition and other characteristics of these participants have been published elsewhere (Halvatsiotis et al. (2002) *Diabetes* 51:2395–2404). All female subjects were studied during the luteal phase. Subjects were provided with a weight-maintaining diet throughout the study. During the I– phase of the study, subjects were withdrawn from antidiabetic treatments for 11 days before biopsy, and during the I+ phase, subjects were treated with four daily injections of regular human insulin doses based on blood glucose values for 11 days before biopsy. The evening before each muscle biopsy, subjects were placed on an intravenous insulin drip in order to negate the effect of hyperglycemia and maintain blood sugars of 80–100 mg/dl during both phases of the study. Muscle biopsy samples of the vastus lateralis were obtained under local anesthesia using a Bergstrom needle (Nair et al. (1988) *Am. J. Physiol.* 254:E208–213).

Human Myosin Heavy Chain Expression: To determine protein content, muscle samples were homogenized in a buffer containing 175 mM KCl, 10 mM Tris.HCl, and 2 mM EDTA, pH 7.2. Samples were briefly centrifuged at 700×g and the pellet was washed twice before being placed in Laemlli sample lysis buffer. Individual samples were separated by electrophoresis on 8% acrylamide gels as described (Talmadge and Roy (1993) *Appl. Physiol.* 75:2337–2340). Gels were silver stained, dried and bands were quantified by densitometry (Giulian et al. (1983) *Anal. Biochem.* 129: 277–287). The relative composition of the type I, IIa, and IIx myosin heavy chain was determined.

Mixed Meal Test: Following an overnight fast, a mixed meal was given in the form of a milk shake containing 25 kcal/kg fat-free mass (pre-determined using dual-energy X-ray absorptiometry). The macronutrient composition of the meal was 55% carbohydrate, 30% fat and 15% protein. The meal was consumed over a 30-minute period while lying in a semi-recumbent position. Subjects remained in this position throughout the study. Arterialized blood samples from a heated hand vein (Copeland et al. (1992) *Am. J. Physiol.* 263:E1010–E1014) were obtained at baseline and then every 30 minutes for five hours after completing the meal.

Plasma insulin was measured with a two-site immunoenzymatic assay (ACCESS® Immunoassay System, Beckman Coulter, Inc. Miami, Fla.). Glucose was measured with a Beckman Glucose Analyzer (Beckman Coulter, Inc.).

Quantitative PCR Analysis: A real time quantitative polymerase chain reaction (PCR) system (Applied Biosystems, Foster City, Calif.) was used to measure the abundance of mRNAs in muscle tissue. RNA was extracted from skeletal muscle of individual subjects using TRIZOL® (Invitrogen Life Technologies), treated with DNase (Invitrogen Life Technologies), and then reverse-transcribed using the Taq-Man Reverse Transcription Reagents (Applied Biosystems). The primer and probe sequences used for human MHCI, MHCIIa, and MHCIIx have been described previously (Balagopal et al. (2001) *Am. J. Physiol. Endocrinol. Metab.* 280:E203–E208). The primer and probe sequences used for the mouse mitochondrial ND1 region were: forward primer: 5'-AAGGAGAATCAGAAT TAGTATCAGGGTT-3' (SEQ ID NO:1); reverse primer: 5'-TGTACTCTGCTATAAAGA ATAACGCGAAT-3' (SEQ ID NO:2); and probe: 5'-ACG-TAGAATACGCAGCCGGCC-3' (SEQ ID NO:3). The primer and probe sequences used for mouse 28S rRNA have been described previously (Balagopal et al., supra). Samples were run in triplicate and quantified by normalizing the target signal for the 28S rRNA signal in each sample.

Cloning the full-length myosin heavy chain I cDNA: Total RNA was isolated from rat soleus muscle and reverse transcribed into cDNA using M-MuLV reverse transcriptase (Roche, Mannheim, Germany). Overlapping fragments of rat myosin heavy chain I cDNA were generated by polymerase chain reaction (PCR) using Platinum Pfx polymerase (Life Technologies, Rockville, Md.) and the following primers: fragment 1 forward 5'-AAGAATTCCCGCTCAGT-CATGGCGGATCGAGAGAT-3' (SEQ ID NO:4), reverse 5'-CCTTGTTCTCTGTTGCGTGCTTTTCCT-3' (SEQ ID NO:5); fragment 2 forward 5'-CAAACTGGAAGAC-GAGTGCTCAGAGCT-3' (SEQ ID NO:6), reverse 5'-TTGTCGAAGTTCCTCTGCTTCTTGTCC-3' (SEQ ID NO:7); fragment 3 forward 5'-AGAACGAGATCGAG-GACCTGATGGTGG-3' (SEQ ID NO:8), and reverse 5'-TCACAGGCATCCTTAGGGTTGGGTAGC-3' (SEQ ID NO:9). Reactions contained 0.3 mM dNTPs, 1 mM magnesium sulfate, 10 µM each primer, 1× amplification buffer, 2 units Pfx polymerase, and 100 pg reverse transcribed cDNA. The resulting fragments were each ligated into a pBluescript II cloning vector (Stratagene, La Jolla, Calif.). To differentiate endogenous myosin heavy chain I from transgene myosin heavy chain I, unique sequence was added to the 3' end of the cDNA by performing an additional amplification on fragment 3 using the same forward primer but the following reverse primer: 5'-GCAAGCTTGCTACT-TGTCGTCGTCCTTGTAGTCCTCTTCATTC AGGCCCT-TGGCGCCAA-3' (SEQ ID NO:10). This product was then ligated into the cloning vector. The cDNA fragments were excised from the cloning vector and ligated together at the overlapping restriction sites to create a full-length cDNA. This product was then put back into the cloning vector. The full-length clone was sequenced in its entirety.

Generation of transgenic mice: Myosin heavy chain 1 complementary cDNA was placed in the previously described myosin light chain-2 promoter minigene vector (Marshall et al. (1993) *J. Biol. Chem.* 268:18442–18445). Slow myoHCI mice were generated by standard DNA microinjection and identified by PCR-based genotyping. For quantitative PCR, total RNA was isolated using TRIZOL® (Molecular Research Center, Cincinnati, Ohio), reverse transcribed using random primers, and analyzed using specific primer and probe sets on an ABI Prism 7700 Sequence Detector (PE Biosystems, Foster City, Calif.).

Western blots: For protein expression analysis, muscles were dissected from age and weight matched wild-type or transgenic FVB mice and frozen in liquid nitrogen. Muscle groups were weighed and homogenized in a pH neutral physiologic buffer containing 177 mM KCl, 10 mM Tris-HCl, and 2 mM EDTA (pH 7.2). Whole muscle homogenate samples were prepared for electrophoresis using reducing Laemmli sample buffer (Bio-Rad, Hercules, Calif.). Loading was normalized for tissue weight. Protein lysates were separated on 4–15% gradient SDS-polyacrylamide gels and immunoblotted with specific antibodies diluted in Tris buffered saline with 0.1% Tween 20 (TBS-T). Primary antibodies included monoclonal anti-myosin (1:1,000) (skeletal, slow; clone NOQ7.5.4D; Sigma, St. Louis, Mo.), anti-myosin heavy chain 2 (1:10,000) (skeletal, fast; clone MY-32; Sigma), anti-actin (1:500) (clone C-2; Santa Cruz Biotechnology, Santa Cruz, Calif.), mouse anti-OxPhos complex II (1:2,000) (Molecular Probes, Eugene, Oreg.), and rabbit anti-PGC-1 (1:1,000) (Chemicon, Temecula, Calif.). Secondary antibodies included horseradish peroxidase-(HRP-)labeled anti-mouse and anti-rabbit antibodies (Amersham, Little Chalfont, Buckinghamshire, England) and HRP-labeled anti-goat (Santa Cruz Biotechnology). These were used at 1:5,000 in TBS-T. Blots were developed using the ECL detection system (Amersham).

For COXI and citrate synthase western blots, muscle samples were homogenized 30× in HES buffer: 20 mM HEPES, 1 mM EDTA, 250 mM sucrose. Triton X-100 (0.1%) and a protease inhibitor cocktail were added. Samples were incubated on ice for 30 minutes and then centrifuged for 20 minutes at 720×g. Supernatants were run on a 10% polyacrylamide gel (Criterion, BioRad), transferred, blocked in 5% milk/TBS-T, and incubated overnight with primary antibody. Primary antibodies against citrate synthase (Chemicon) and COXI (Molecular Probes) were diluted 1:1,000. Secondary HRP-anti-mouse antibody (1:10, 000) and ECL substrate were used for detection. A Kodak Image Station 1000 was used for scanning and densitometry. Citrate synthase assays were performed on supernatants from muscle samples prepared as described above. Enzyme activity was measured using a spectrophotometric assay (Short et al. (2003) *Diabetes* 52:1888–1896).

Metachromatic and immunofluorescent staining: Skeletal muscle was collected, embedded in tragacanth gum and frozen in isopentane cooled in liquid nitrogen. Five-micrometer-thick serial frozen sections were obtained and processed for staining. Metachromatic ATPase staining was performed as described (Ogilvie and Feeback (1990) *Stain Technology* 65:231–241). Immunofluorescent staining was performed with antibodies specific for slow myoHCI (NOQ7.5.4D, Sigma, St. Louis, Mo.), fast myosin heavy chain (MY-32, Sigma), and slow TnI (sc-8119, Santa Cruz Biotechnology, Inc.).

Glucose tolerance tests, insulin assays, activity, and DXA analysis: Wild-type and transgenic littermates were fasted overnight and then given a 2 g/kg oral glucose load. Glucose concentration was measured in tail vein samples at designated times. Baseline insulin levels were measured on tail vein blood samples after a 4-hour fast using a rodent insulin radio-immunoassay (Linko, St. Charles, Mo.). An infrared photocell device (Opto-Varimex, Columbus Instruments, Korea) was used to measure spontaneous physical activity over a 24-hour period. DXA scanning and analysis was done on a PIXImus scanner (Lunar, Wheeling, Ill.).

Glycogen and glycogen synthase quantification: Six to eight-week old mice were fasted overnight prior to muscle harvest. For glycogen measurements muscles were heated in 2 N hydrochloric acid and then neutralized by the addition of sodium hydroxide. Quantification was conducted by the hexokinase spectrophotometric method using Infinity Reagent™ (ThermoTrace, Australia). For glycogen synthase, muscle was homogenized in ice-cold glycogen synthase buffer containing a reducing agent and protease inhibitor. Supernatants were used for measurement of "active" and "total" glycogen synthase activity. Enzyme activity was assayed by measuring the incorporation of $^{14}$C-glucose from uridine diphospho-$^{14}$C-glucose into glycogen either in the presence or absence of 10 mM glucose-6-phosphate.

Statistical Analyses: Data are reported as mean±SEM. Differences were analyzed using unpaired t-tests. A P-value<0.05 was considered statistically significant.

Example 2

MHC Levels in Human Subjects

Levels of messenger RNA (mRNA) and protein for various isoforms of MHC were evaluated in muscle samples from young (21–38 years) and older (60–87 years) human subjects. Muscle mRNA levels for fast myoHC isoforms IIA and IIX were significantly lower in the older subjects than in younger subjects, while MHCI levels were unchanged (FIG. 1*a*). MyoHC protein levels were then quantified by electrophoretic separation. Older subjects had a predominance of slow-twitch MHCI and significantly less fast-twitch MHCIIX compared to young subjects (FIG. 1*b*), consistent with the observation that older individuals have proportionally more slow-twitch muscle than younger individuals (Lexell et al. (1988) *J. Neurol. Sci.* 84:275–294).

To examine the impairment of glucose metabolism that can occur with aging, plasma glucose and insulin levels were measured after overnight fasting and following a meal in young and older human subjects. After the meal, the older people had higher peak glucose levels at 30 minutes, and maintained 15–20% higher blood glucose concentrations than young people for up to 5 hours (FIG. 1*c*). However, insulin levels were not statistically different between young and older subjects at baseline or following the meal (FIG. 1*d*). Thus, older people had a normal insulin response to the meal but were resistant to the effects of insulin. Skeletal muscle is the major site of glucose uptake after a meal, and therefore a major regulator of post-meal blood glucose levels. Thus, these results suggest an important association between the relative increase in MHCI in older subjects and the impairment of glucose disposal after a mixed meal.

Since MHC isoform levels and glucose disposal are both known to be affected by physical activity, weekly activity was quantified in all subjects using the Minnesota Leisure Time Activity Questionnaire (Taylor et al. (1978) *J. Chron. Dis.* 31:741–755). There was no difference between younger and older subjects in the physical activity score, with older individuals reporting 224±35 activity metabolic units per week and younger individuals reporting 225±34 activity metabolic units per week. Thus, the observed increase in slow-twitch muscle and the impairment of glucose disposal were not likely the result of major differences in physical activity between younger and older subjects.

Example 3

Generation and Characterization of Transgenic Mice

To generate mice that have more slow-twitch muscle, the myosin light chain 2 promoter (MLC 2) was used to over-express slow myosin heavy chain 1 (slow myoHCI) in skeletal muscle. This promoter has been shown to induce gene expression 6 days after birth (Shani et al. (1988) *Mol. Cell. Endocrinol.* 8:1006–1009), approximately when muscle fiber types are being established (Weiss et al. (1999) *Proc Natl. Acad. Sci. USA* 96:2958–2963). To ensure that any observed effects were due to slow myoHCI over-expression and not to integration site effects, two independent founder lines were propagated for further study.

Western blotting of total cell lysates with an antibody specific for slow myoHCI revealed that transgene expression was muscle-specific. Further, Western blots performed to quantify the increase in slow myoHCI expression in the transgenic mice demonstrated a 2.8-fold increase in slow myoHCI expression in the quadriceps muscle (FIG. 2a). No effect of transgene expression was observed in the soleus, presumably because this muscle is composed predominantly of slow-twitch fibers.

Using quantitative PCR with primer sets designed to amplify either total myoHCI (endogenous and transgene) or transgene-specific primers, the levels of both endogenous myoHCI expression and transgene myoHCI expression were established. Total myoHCI expression was increased in transgenic mice compared to their control littermates. In the quadriceps muscle for example, a 2.6±0.6 ($p<0.005$) fold increase in myoHCI mRNA relative to 28S rRNA was observed with no detectable change in myoHCIIx mRNA expression.

Figure 2B:
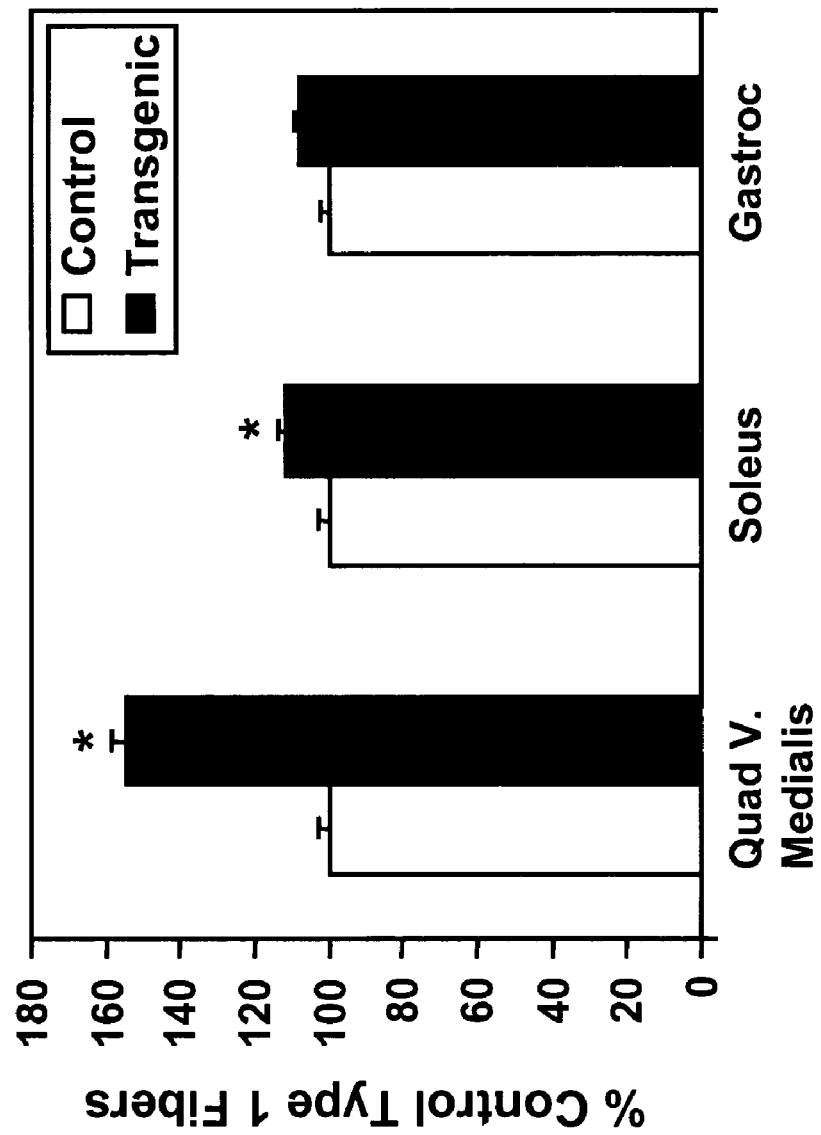
FIG. 2b is a graph showing the relative amounts of slow-twitch (type 1) muscle fibers in transgenic mice (solid columns) vs. control mice (open columns). Quad V. Medialis, quadriceps vastus medialis; Gastroc, gastrocnemius; *, p<0.046.

The traditional means for distinguishing muscle fiber types histologically is metachromatic ATPase staining. This method differentiates muscle fiber types by the unique pH sensitivity inherent to each isoform of myosin. Slow myoHCI is inactivated at an alkaline pH, while the fast myosin isoforms maintain their ATPase activity and stain darkly. This technique was used to determine whether the increased expression of slow myoHCI resulted in increased slow-twitch muscle fibers. In addition, immunofluorescence with an antibody specific for slow myoHCI was used to quantify slow-twitch muscle fibers on frozen muscle sections. A 55% increase in slow-twitch fibers was detected in quadriceps muscles from transgenic animals (FIG. 2b). Although not detectable by Western blotting (possibly because of the normal predominance of myoHCI expression), a 12% increase in slow-twitch fibers was demonstrated in histologic sections of soleus muscle.

Fluorescent visualization of quadriceps muscle sections stained with the anti-slow myoHCI antibody revealed a substantial increase in positive fibers, particularly in the vastus medialis. In addition, the ATPase activity in the slow myoHCI positive fibers was consistent with slow-twitch fibers. To further confirm that these were indeed slow-twitch fibers, they were stained with an antibody specific the slow isoform of troponin I (TnI slow), which is unique to slow-twitch fibers. The slow myoHCI positive fibers also were positive for TnI slow. Furthermore, no staining was observed in slow myoHCI fibers with an antibody specific for fast myosin isoforms. The ATPase staining, slow myoHCI staining, TnI slow staining, and lack of fast myosin isoform staining provided convincing evidence that these were indeed slow-twitch muscle fibers. Thus, over-expression of slow myoHCI drove fibers to express the other complimentary slow-twitch fiber-specific proteins.

Figure 3A:
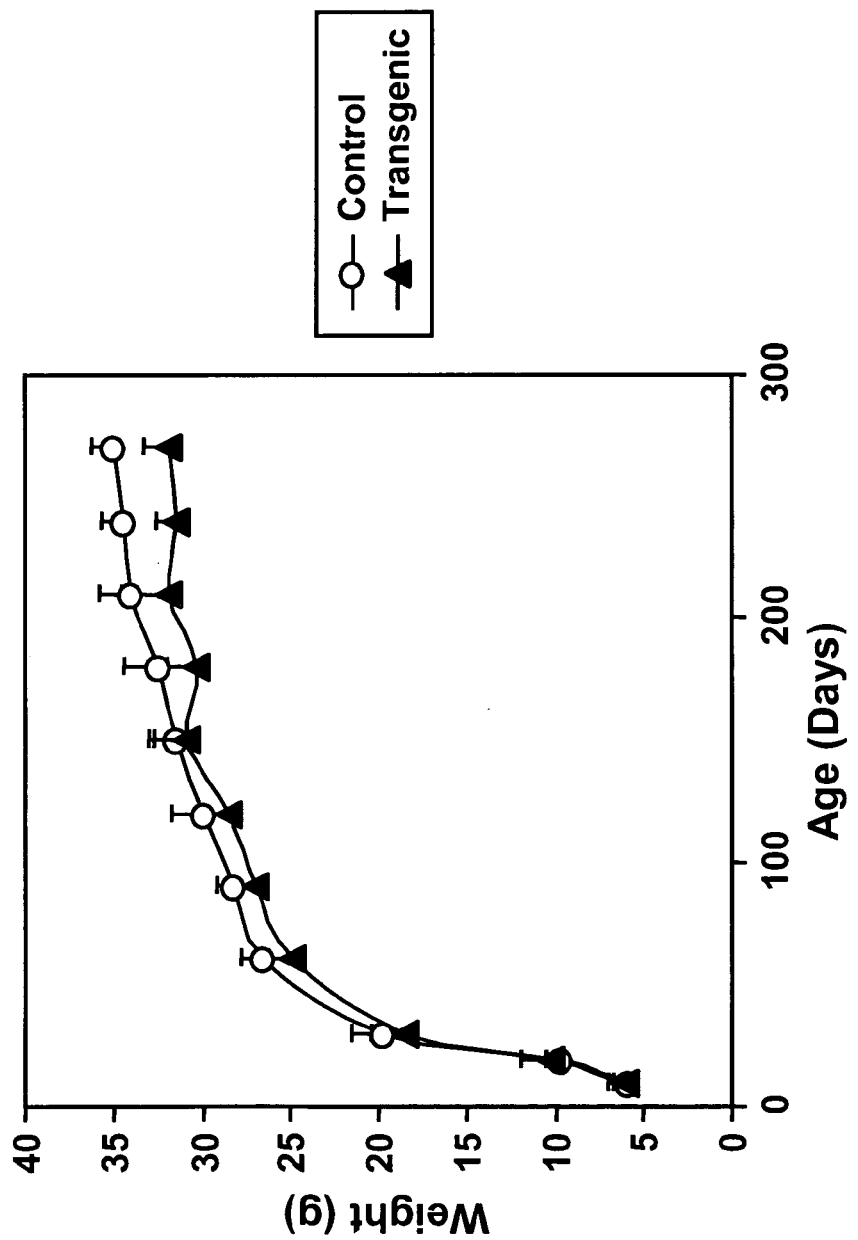
FIG. 3a is a graph plotting the weights of slow myoHCI transgenic mice (filled triangles) vs. their control wild type littermates (open circles).

Since muscle strength and structure can alter bone growth and maintenance, experiments were conducted to determine whether the shift toward more slow-twitch muscle fibers would result in any skeletal changes. Scanning by dual X-ray absorptiometry (DXA) indicated that there were no apparent differences in skeletal structure or bone mineral content in transgenic mice as compared to control littermates. In addition, the growth rates of transgenic mice also were examined. These studies revealed that the shift in muscle fiber type did not result in any change in total body weight in the slow myoHCI mice as compared to control littermates (FIG. 3a).

Figure 3B:
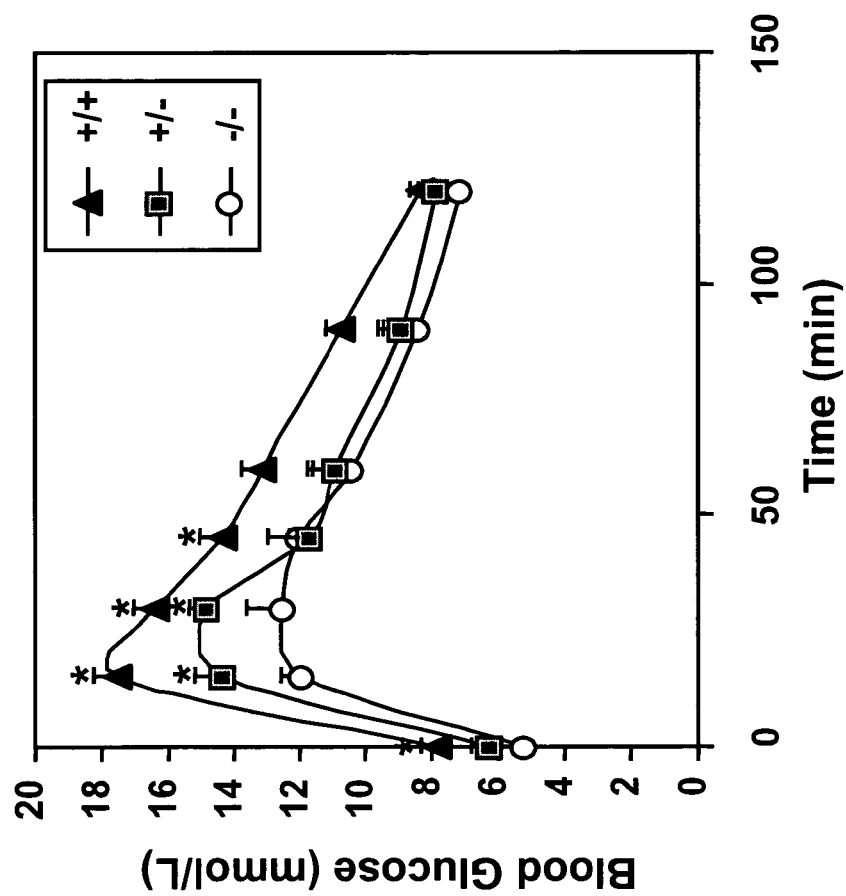
FIG. 3b is a graph showing blood glucose levels after oral glucose tolerance testing of control mice (−/−, open circles) and their transgenic littermates (−/+ and +/+; filled squares and filled triangles, respectively). *, p<0.03.
Figure 3C:
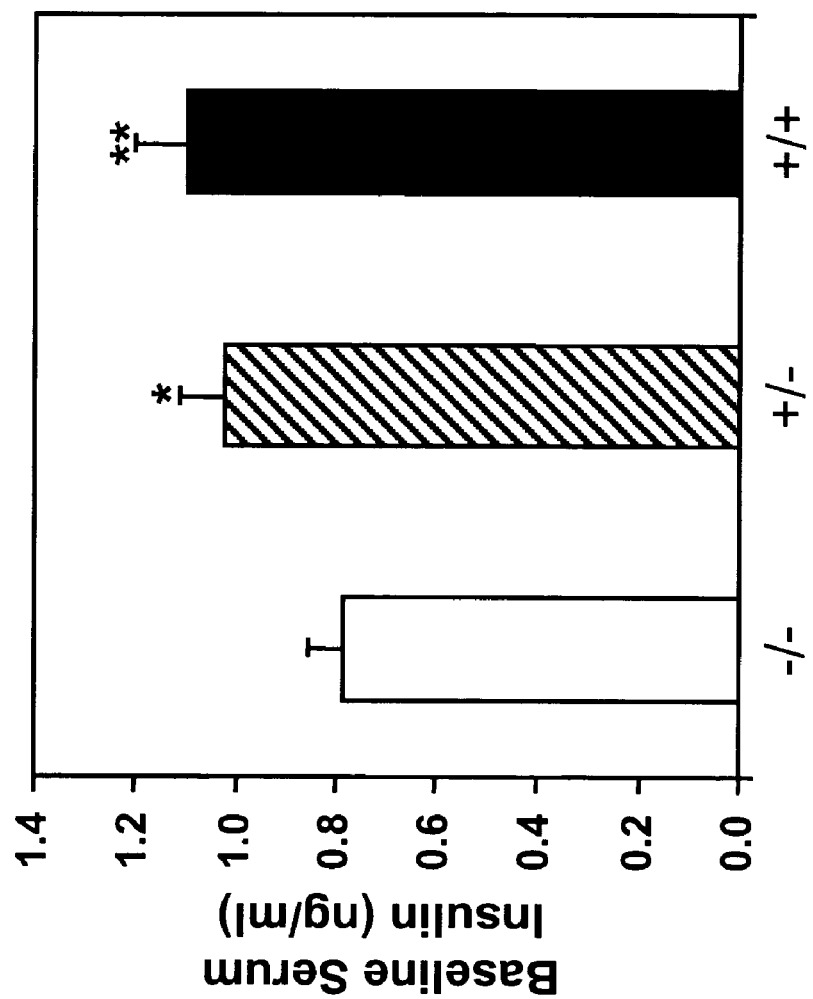
FIG. 3c is a graph plotting insulin levels in control mice (−/−) and transgenic littermates (−/+ and +/+) as indicated. *, p<0.03; **, p<0.004.

Skeletal muscle is the major organ involved in the disposal of glucose, especially following a meal. To examine the effect of increased slow-twitch muscle on glucose metabolism, oral glucose tolerance testing was performed on mice that were fasted overnight. The mice were used for these studies at 6–7 weeks of age, when they are expected to have normal glucose metabolism that is unaffected by aging, thus allowing assessment of the myoHCI effect independent of other aging-related changes that might occur in the skeletal muscle of older mice. The baseline fasting blood glucose value was 40% higher in the transgenic mice than in control littermates (FIG. 3b). Following consumption of glucose, the transgenic animals showed significantly elevated blood glucose concentrations as compared to control littermates, consistent with impaired glucose tolerance. These data were independently confirmed by intraperitoneal glucose tolerance testing. Serum insulin levels were measured to determine whether the elevated blood glucose in transgenic mice was due to impaired insulin secretion or to insulin resistance. In the baseline state, serum insulin levels of transgenic mice were higher that those of control mice (FIG. 3c). The presence of increased blood glucose levels despite increased insulin levels indicate insulin resistance, thus demonstrating that the transgenic mice had impaired glucose tolerance because of insulin resistance. These findings are consistent with the observations in older humans (FIGS. 1c and 1d).

Figure 3D:
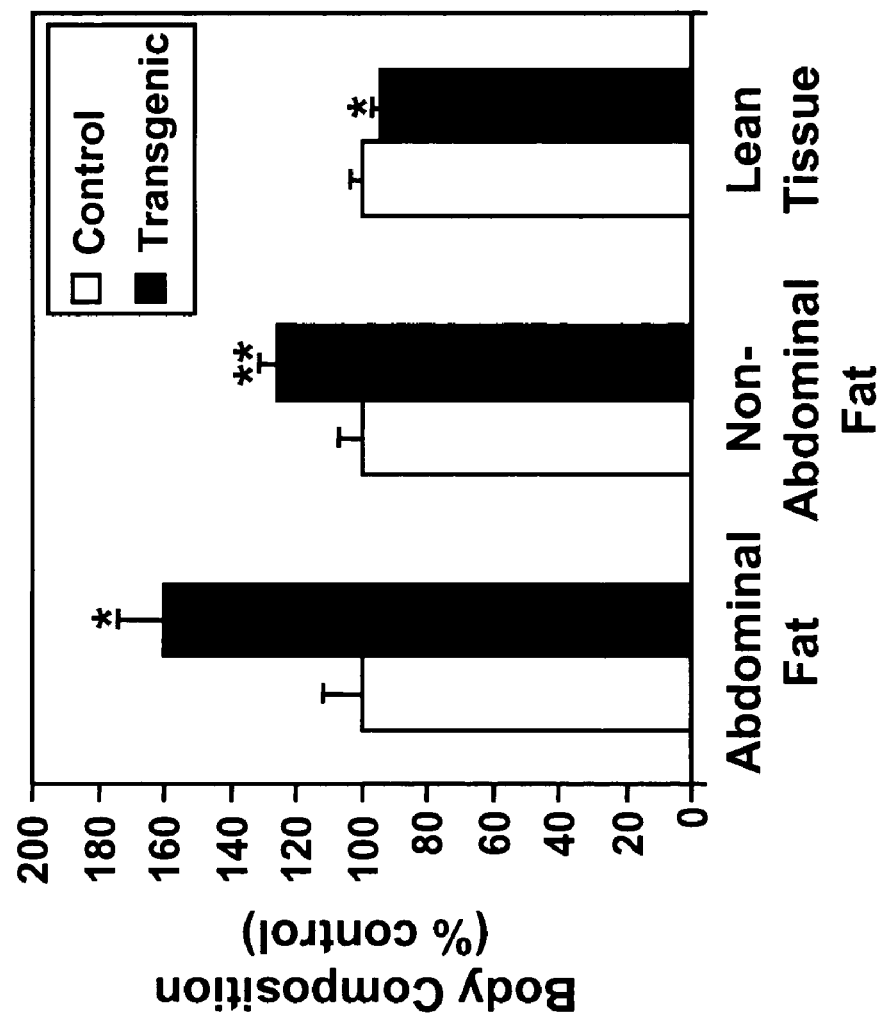
FIG. 3d is a graph plotting body composition of control mice (open columns) vs. slow myoHCI littermates (solid columns). *, p<0.005; **, p<0.01.

The impaired glucose tolerance observed with aging is associated with accumulation of intra-abdominal fat, although a direct mechanism remains to be established. In Zucker Diabetic Fatty rats that are obese and accumulate intra-abdominal fat, surgical removal of the fat significantly improves glucose utilization (Gabriely et al. (2002) *Diabetes* 51:2951–2958). Dual energy x-ray absorptiometry (DXA) scanning and direct dissection were used to measure intra-abdominal fat and assess body composition in transgenic and control mice. DXA scanning revealed that although there were no differences in body weight between the two groups, transgenic mice had more fat and less lean tissue than control mice. In addition, there was a particular increase in intra-abdominal fat (FIG. 3d). The DXA data were confirmed by direct dissection and weighing of all visible intra-abdominal fat.

Since muscle strength and structure can alter bone growth and maintenance, experiments were conducted to determine whether the shift toward more slow-twitch muscle fibers resulted in any skeletal changes. DXA scanning was used for detailed visualization of the skeleton and for quantification of bone mineral content. No differences in skeletal structure or bone mineral content were observed in transgenic mice as compared to control littermates.

Food consumption was measured over a 7 day period to determine whether the slow myoHCI mice were eating more than the control mice. However, there were no differences in the amount of food consumed by control mice versus transgenic mice (33.4 g±2.2 g, n=14 vs. 33.6 g±3.6 g, n=14). Thus, the differences in body composition were due not to differences in food consumption, but to inherent differences in the way calories were being partitioned once consumed.

Figure 4:
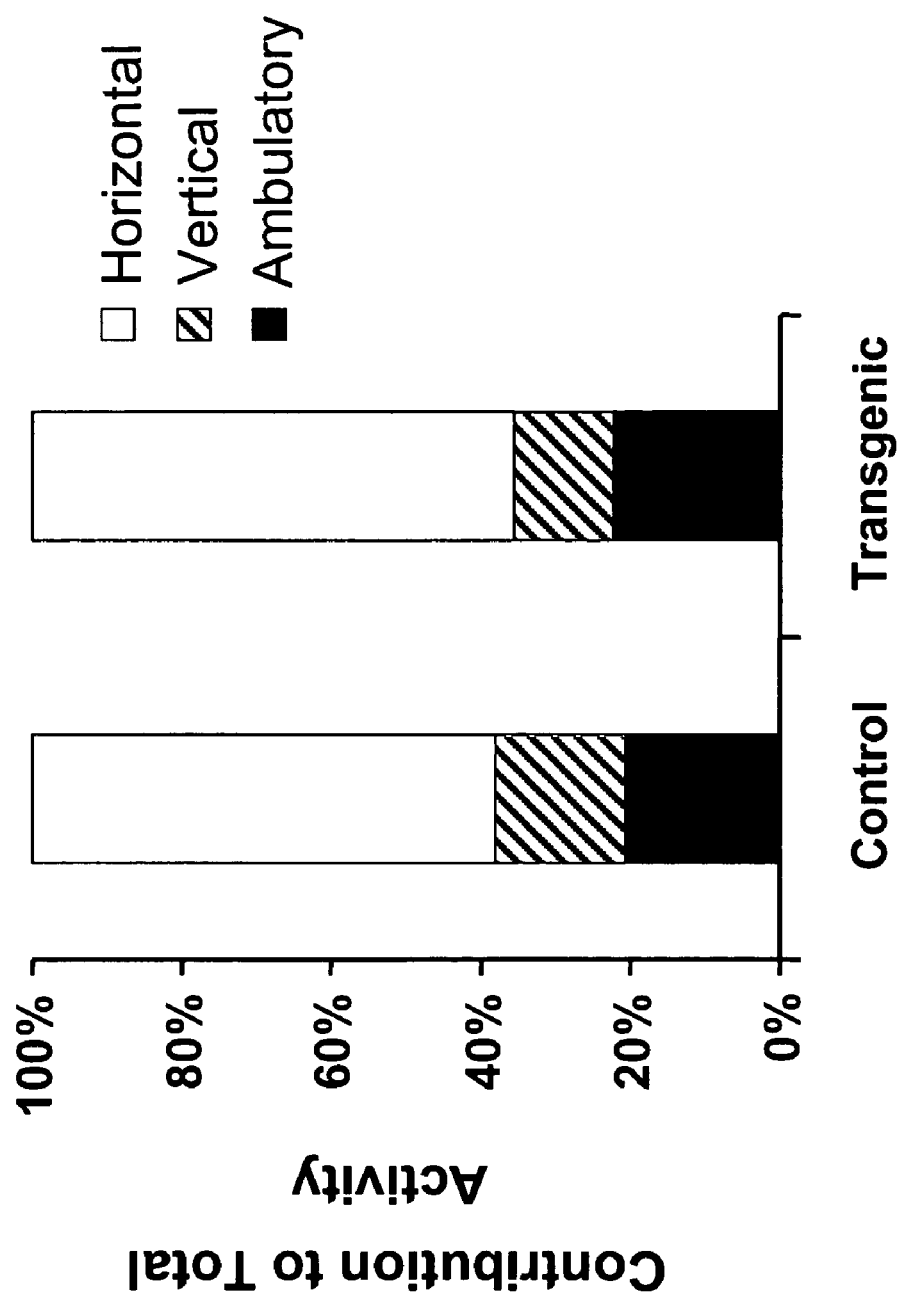
FIG. 4 is a graph plotting levels of spontaneous physical activity as indicated in control mice vs. slow myoHCI transgenic mice.

Metabolic defects in glucose metabolism and increased fat accumulation are more commonly observed in sedentary individuals, and it is well established that exercise can improve glucose tolerance and reduce body fat. Food intake and physical activity levels of the transgenic and control mice were measured to determine whether the slow myoHCI mice were physically less active or consumed more calories. Food consumption was measured over a 7 day period. Spontaneous physical activity, including vertical, horizontal, and ambulatory movements, was measured with an array of infrared sensors (Levine et al. (2002) *J. Appl. Physiol.* 94:165–170) over a 24-hour period. These studies showed that food intake was similar for control (4.77±0.31 g/day, n=14) and transgenic (4.80±0.51 g/day, n=14) mice. Likewise, there was no significant difference in activity levels between transgenic and control mice (8.1±1.8 total activity units for transgenic mice, n=9 vs. 6.1±2.0 total activity units for control mice, n=9) (FIG. 4). Thus, neither increased caloric intake or inactivity could explain the higher body fat or the defect in glucose metabolism in the transgenic mice.

Figure 5:
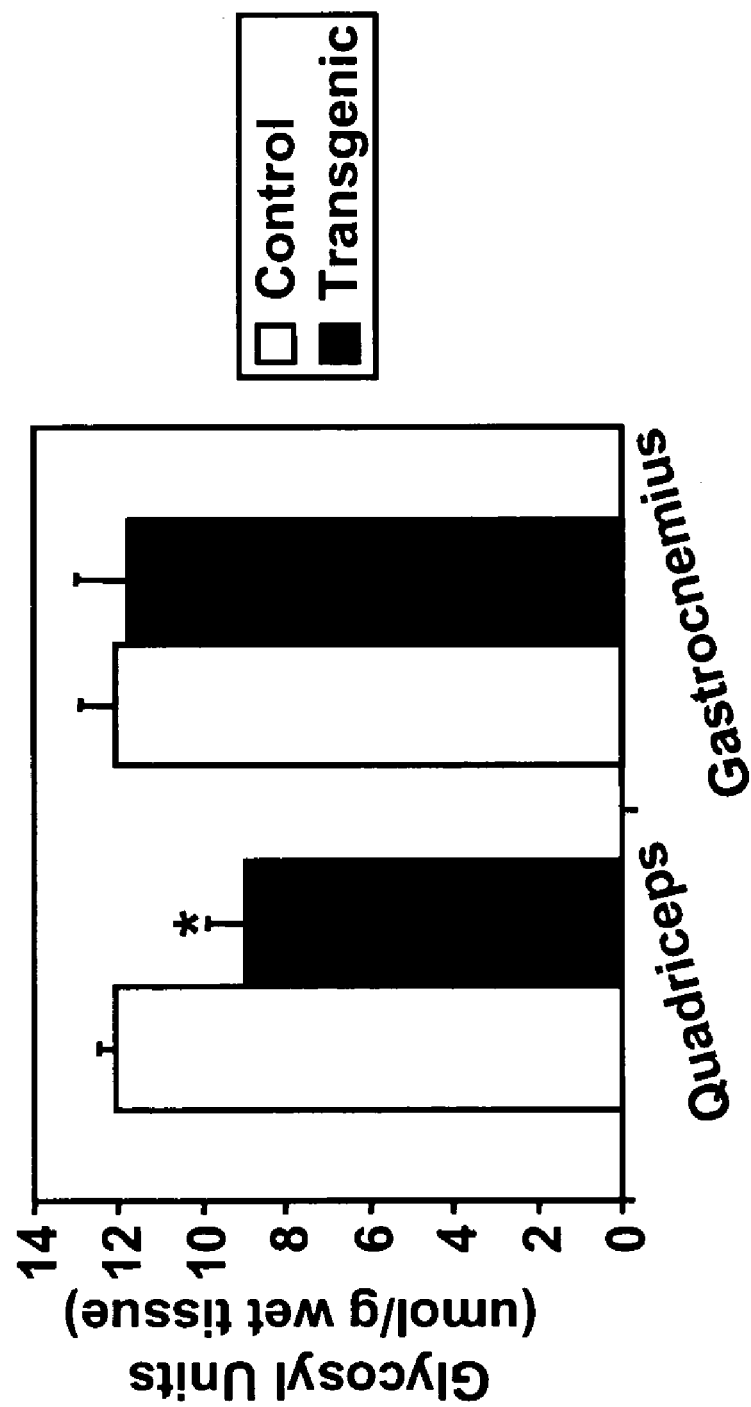
FIG. 5 is a graph showing the glycogen content in the quadriceps and gastrocnemius muscles of transgenic mice (solid columns) vs. control mice (open columns). *, p<0.01.

Once glucose enters the muscle it either is metabolized to produce ATP or it is stored as glycogen for later use. Measurements of glycogen accumulation by $^{13}$C-NMR spectroscopy in human muscle following a meal suggest that the majority of glucose taken up into a muscle cell is stored as glycogen rather than oxidatively metabolized (Schulman et al. (1990) *New Engl. J. Med.* 322:223–228). The slow myoHCI mice showed a particular defect in post-prandial glucose utilization, indicating that storage of glycogen may have been impaired with the shift toward more slow-twitch muscle. Indeed, measurement of muscle glycogen demonstrated that in the quadriceps muscle, where there was a significant increase in slow-twitch muscle, transgenic mice stored almost 30% less muscle glycogen than controls. In the gastrocnemius muscle, where there was no increase in slow-twitch muscle, glycogen content was not different between transgenic and control mice (FIG. 5). Thus, a shift toward slow-twitch muscle fiber type led to less glycogen storage and, as a consequence was associated with impaired glucose tolerance.

Figure 6A:
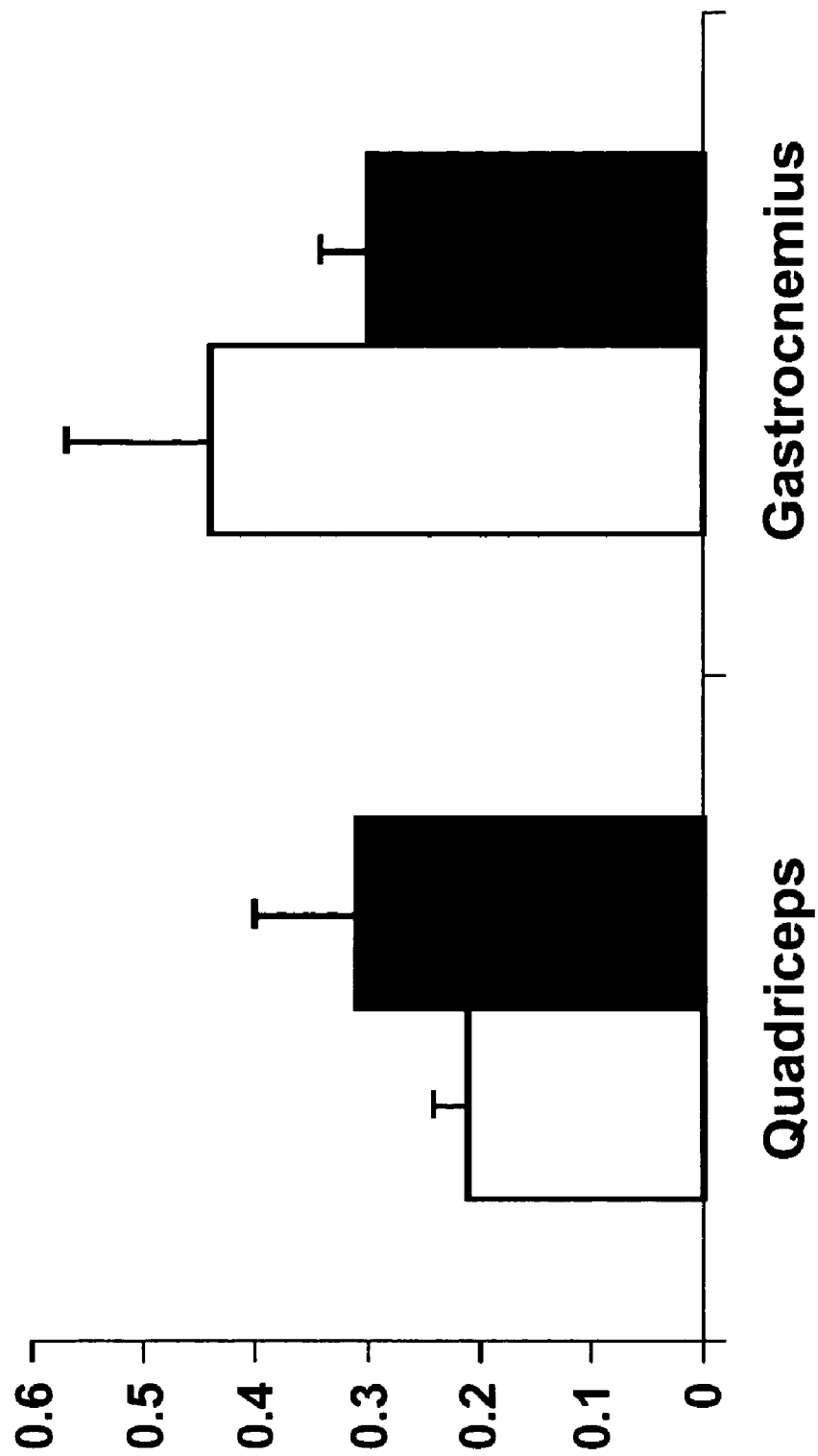
FIG. 6a is a graph showing the level of PGC-1 mRNA normalized to 28S rRNA content in the quadriceps and gastrocnemius muscles of transgenic mice (n=5, solid columns) vs. control mice (n=7, open columns).
Figure 6B:
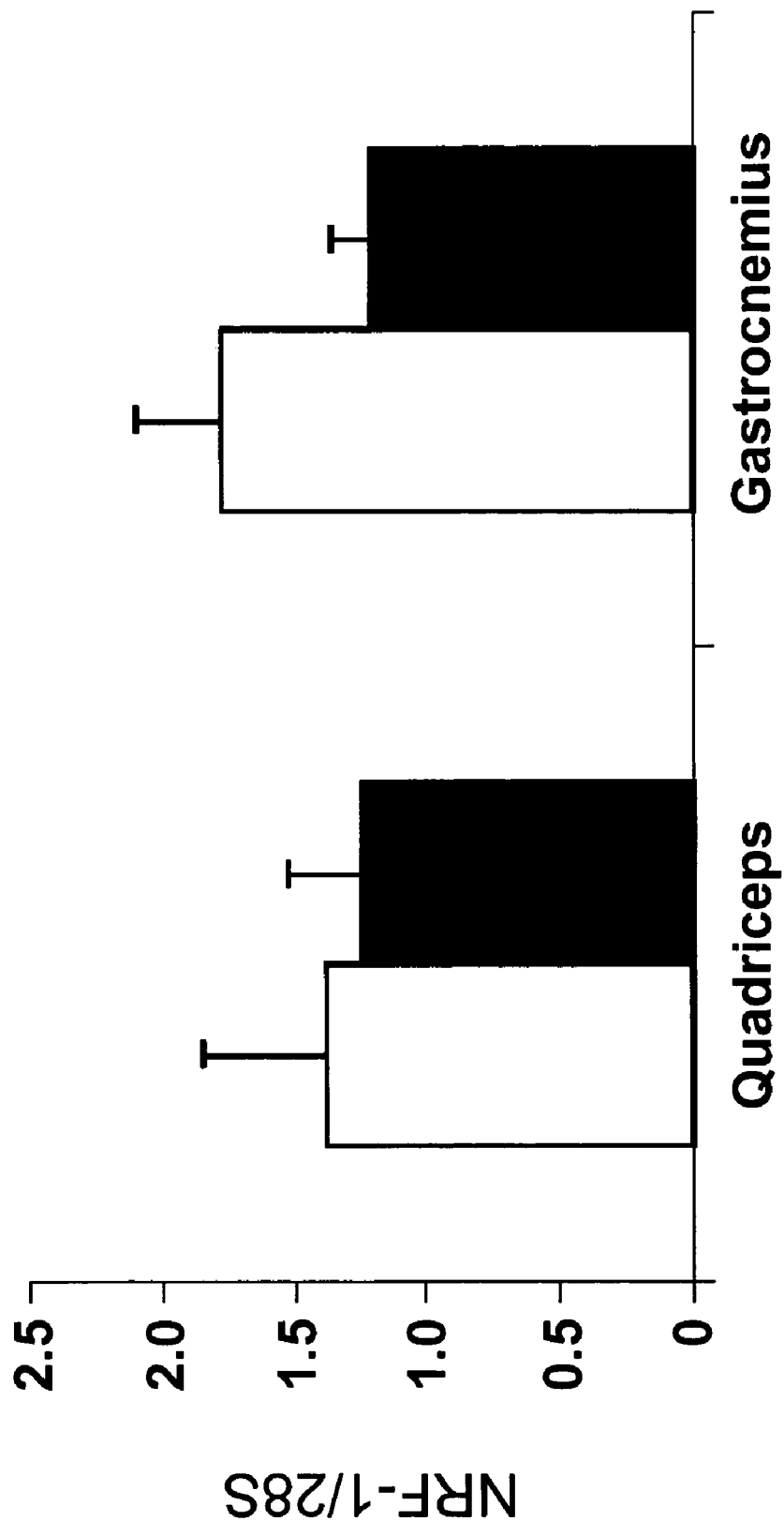
FIG. 6b is a graph showing the level of NRF-1 mRNA normalized to 28S rRNA content in the quadriceps and gastrocnemius muscles of transgenic mice (n=5, solid columns) vs. control mice (n=7, open columns).

In slow-twitch muscle fibers, mitochondrial numbers are higher and more ATP is produced by oxidative phosphorylation (Thorstensson and Karlsson (1976) *Acta Physiol. Scand.* 98:318–322; Cusso et al. (2003) *Biochim. Biophys. Acta.* 1620:65–71; and Derave et al. (2000) *Am. J. Physiol. Endocrinol. Metab.* 279:E947–955). The transcriptional co-activator PGC-1α and the transcription factor nuclear regulatory factor-1 (NRF-1) are important regulators of mitochondrial biogenesis (Hood (2001) *J. Appl. Physiol.* 90:1137–1157; and Scarpulla (2002) *Gene* 286:81–89). Quantitative PCR was used to measure the mRNA levels for these proteins (FIGS. 6a and 6b). In the quadriceps as well as the gastrocnemius/plantaris, there was no significant difference between control and transgenic mice in PGC-1α or NRF-1 mRNA levels. PGC-1α protein levels also were assessed by Western blotting and were not found to be different.

Muscle mitochondrial content was assessed using quantitative PCR to measure mitochondrial DNA copy number. Using primers designed to specifically amplify the mitochondrial genomic ND1 (the mitochondrial region encoding subunit 1 of complex I) and by comparing this to the 28S rRNA content, a ratio of mitochondria per 28S rRNA was determined. This ratio was measured in both the quadriceps and gastrocnemius/plantaris muscle of control mice (n=7) and transgenic mice (n=5), and no statistical difference was observed (FIG. 7a).

Figure 7B:
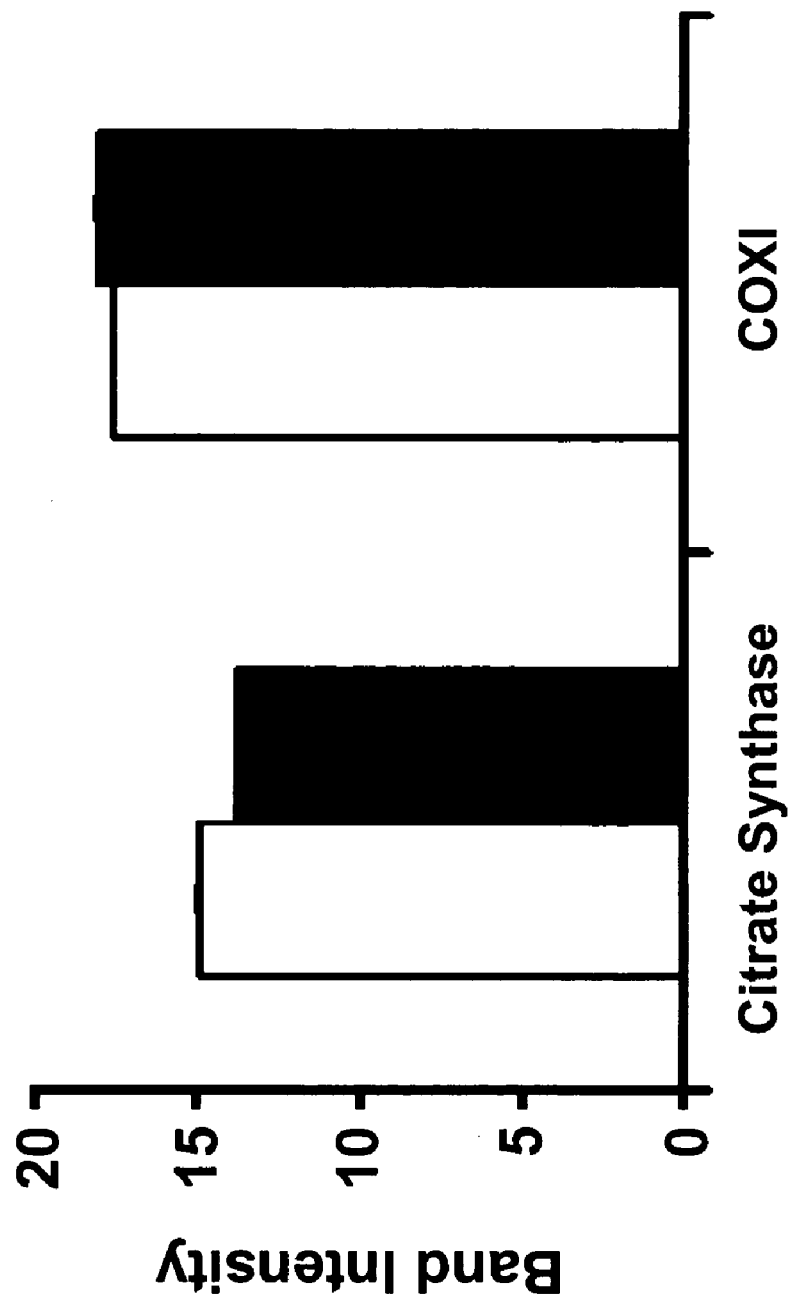
FIG. 7b is a graph showing the levels of mitochondrial citrate synthase and cytochrome C oxidase I (COXI) protein in quadriceps of transgenic mice (n=8, solid columns) vs. control mice (n=5, white bars).

Mitochondrial content was further quantified by Western blot using antibodies specific for mitochondrial citrate synthase or for COXI. There was no difference in citrate synthase or COXI protein levels in lysates from the quadriceps muscle of control or transgenic mice (FIG. 7b). Western blots for mitochondrial oxidative phosphorylation complex II protein content also showed no differences between control and transgenic mice. Mitochondrial function was further assessed by measuring citrate synthase enzymatic activity in quadriceps muscle. Again, no differences were observed between control and transgenic mice (FIG. 7c). Thus, although more muscle fibers were expressing characteristic slow-twitch contractile proteins, mitochondrial numbers were not increased as a result.

Example 4

Insulin Effects on Expression of MHC Isoforms

Figure 8:
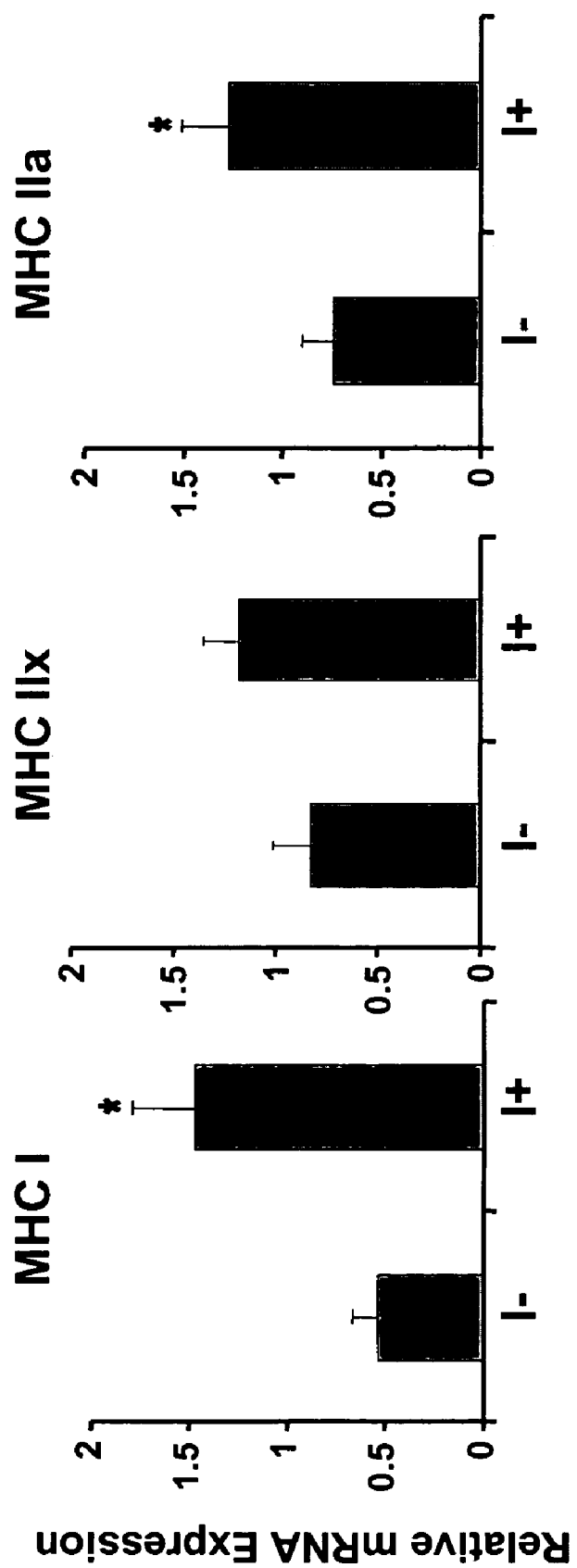
FIG. 8 is a series of graphs showing mRNA levels of the indicated MHC isoforms in skeletal muscle of insulin deficient (I−) and insulin treated (I+) diabetic subjects.

Since increased MHCI was associated with skeletal muscle insulin resistance in human subjects and in the myoHCI transgenic mice, the effect of insulin on expression of MHC isoforms was evaluated in human type 2 diabetic subjects. Eight type 2 diabetic subjects were maintained for 11 days without therapy. After this initial period, skeletal muscle biopsy samples were collected and mRNA was isolated for analysis. To measure effect of insulin, the same 8 subjects were studied after intensive insulin therapy. Quantitative PCR revealed a 2.7-fold increase in MHCI expression in response to insulin therapy. In contrast, only a 1.7 fold increase in fast MHCIIa was observed, and there was no change in fast MHCIIx (FIG. 8). These data suggested that insulin has a differential effect on MHC isoform expression.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse, the nucleated cells of which comprise a transgene, wherein said transgene comprises a MLC2 promoter operably linked to a nucleic acid encoding a myosin heavy chain-I (MHCI) polypeptide, wherein expression of said nucleic acid results in an increase in the number of slow-twitch muscle fibers in skeletal muscle of said transgenic mouse as compared to the number of slow-twitch muscle fibers in skeletal muscle of corresponding non-transgenic mice.

2. The transgenic mouse of claim 1, wherein said MHCI polypeptide is a rodent MHCI polypeptide.

3. The transgenic mouse of claim 2, wherein said rodent MHCI polypeptide is a rat MHCI polypeptide.

4. The transgenic mouse of claim 2, wherein said rodent MHCI polypeptide is a mouse MHCI polypeptide.

5. The transgenic rodent mouse of claim 1, wherein said MLC2 promoter is a rat MLC2 promoter.

6. The transgenic mouse of claim 1, wherein said mouse displays one or more symptoms or complications of diabetes, wherein said one or more symptoms or complications of diabetes are selected from the group consisting of impaired glucose tolerance, insulin resistance, cardiovascular disorders, ketoacidosis, foot problems, skin problems, infection, slow wound healing, excessive thirst, frequent urination, blurred vision, and fatigue.

7. The transgenic mouse of claim 6, wherein said diabetes is type 2 diabetes.

8. The transgenic mouse of claim 1, wherein muscle mitochondrial content in said transgenic mouse is not significantly different from muscle mitochondrial content in said corresponding non-transgenic mice.

9. A method of screening compounds for effectiveness in treating diabetes, said method comprising:
 (a) providing a candidate compound;
 (b) providing a transgenic mouse, the nucleated cells of which comprise a transgene, wherein said transgene comprises a MLC2 promoter operably linked to a nucleic acid encoding an MHCI polypeptide, wherein expression of said nucleic acid results in an increased ratio of type I muscle fibers to type II muscle fibers in skeletal muscle of said transgenic mouse as compared to the ratio of type I muscle fibers to type II muscle fibers in skeletal muscle of corresponding non-transgenic mice;
 (c) administering said candidate compound to said transgenic mouse; and
 (d) monitoring said transgenic mouse for one or more symptoms or complications of diabetes, wherein said one or more symptoms or complications of diabetes are selected from the group consisting of impaired glucose tolerance, insulin resistance, cardiovascular disorders, ketoacidosis, foot problems, skin problems, infection, slow wound healing, excessive thirst, frequent urination, blurred vision, and fatigue.

10. The method of claim 9, wherein said diabetes is type 2 diabetes.

11. The method of claim 9, wherein said MHCI polypeptide is a rodent MHCI polypeptide.

12. The method of claim 11, wherein said rodent MHCI polypeptide is a rat MHCI polypeptide.

13. The method of claim 11, wherein said rodent MHCI polypeptide is a mouse MHCI polypeptide.

14. The method of claim 9, wherein said MLC2 promoter is a rat MLC2 promoter.

15. The method of claim 9, wherein said monitoring comprises measuring glucose tolerance.

16. The method of claim 9, wherein said monitoring comprises measuring insulin resistance.

17. The method of claim 9, wherein muscle mitochondrial content in said transgenic mouse is not significantly different from muscle mitochondrial content in said corresponding non-transgenic mice.

* * * * *

UNITED STATES PATENT AND TRADEMARK OFFICE
CERTIFICATE OF CORRECTION

PATENT NO. : 7,235,709 B1
APPLICATION NO. : 10/977458
DATED : June 26, 2007
INVENTOR(S) : K. Sreekumaran Nair and Laura J. Greenlund Page 1 of 1

It is certified that error appears in the above-identified patent and that said Letters Patent is hereby corrected as shown below:

Column 23, line 58, please delete "rodent".

Signed and Sealed this

Second Day of September, 2008

JON W. DUDAS
*Director of the United States Patent and Trademark Office*